United States Patent
Shibata et al.

(10) Patent No.: US 7,826,047 B2
(45) Date of Patent: Nov. 2, 2010

(54) APPARATUS AND METHOD FOR OPTICAL INSPECTION

(75) Inventors: Yukihiro Shibata, Fujisawa (JP); Shunji Maeda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 558 days.

(21) Appl. No.: 11/583,892

(22) Filed: Oct. 20, 2006

(65) Prior Publication Data

US 2007/0121106 A1 May 31, 2007

(30) Foreign Application Priority Data

Nov. 29, 2005 (JP) .............................. 2005-343215

(51) Int. Cl.
*G01N 21/00* (2006.01)
(52) U.S. Cl. .................................................. 356/237.2
(58) Field of Classification Search ........................ None
See application file for complete search history.

(56) References Cited

U.S. PATENT DOCUMENTS

| | | | | |
|---|---|---|---|---|
| 4,595,289 A | * | 6/1986 | Feldman et al. | 356/237.5 |
| 5,506,676 A | * | 4/1996 | Hendler et al. | 356/237.1 |
| 6,404,498 B1 | | 6/2002 | Maeda et al. | |
| 6,570,650 B1 | * | 5/2003 | Guan et al. | 356/237.4 |
| 6,777,676 B1 | * | 8/2004 | Wang et al. | 356/237.1 |
| 6,787,773 B1 | * | 9/2004 | Lee | 250/311 |
| 6,867,862 B2 | * | 3/2005 | Nikoonahad | 356/340 |
| 7,239,389 B2 | * | 7/2007 | Baer et al. | 356/369 |
| 7,369,233 B2 | * | 5/2008 | Nikoonahad et al. | 356/237.2 |
| 2007/0081151 A1 | * | 4/2007 | Shortt et al. | 356/237.2 |

FOREIGN PATENT DOCUMENTS

| JP | 08-162511 | 6/1996 |
|---|---|---|
| JP | 2004-087820 | 3/2004 |

\* cited by examiner

*Primary Examiner*—Gregory J Toatley, Jr.
*Assistant Examiner*—Juan D Valentin
(74) *Attorney, Agent, or Firm*—Antonelli, Terry, Stout & Kraus, LLP.

(57) ABSTRACT

The present invention provides a variety of optical functions so as to be applicable to various kinds of objects to be inspected. For each of the optical functions, the invention accumulates contrasts (brightness differences), etc. of defects to be detected (DOI) and false defects not to be detected (nuisance), and efficiently selects parameters advantageous for inspection with high sensitivity and low nuisance ratio. A wavelength band, an illumination scheme, and filtering parameters can be selected for an optical system.

23 Claims, 13 Drawing Sheets

APPARATUS AND METHOD FOR OPTICAL INSPECTION

BACKGROUND OF THE INVENTION

The present invention relates to an apparatus and method for optical inspection of pattern defects, foreign particles, and other foreign substances present on fine patterns formed on substrates through a thin-film forming process represented by a semiconductor manufacturing process or a flat-panel display manufacturing process.

A known conventional apparatus for optical defect inspection is described in Japanese Laid-Open Patent Application Publication No. Hei 08-162511 corresponding to U.S. Pat. No. 6,404,498 B1 (Patent Document 1). The apparatus described in Patent Document 1 includes: a light source capable of illuminating a sample through selection of high intensity illumination with a short wavelength interval using a Hg-Axe lamp and white light illumination using a Axe lamp, using a wavelength (e.g., 600 nm or less) selected via a wavelength selection filter, and emitting annular diffuse illumination light formed by a large number of virtual point light sources; a bright-field illumination optical system adapted to polarize annular diffuse illumination light that has been emitted from the light source via polarization conversion optical element (polarizing beam splitter and a quarter-wave plate), then condense the illumination light through the pupil of an objective lens, and irradiate onto the surface of a pattern formed on an object to be inspected with the condensed illumination light; a dark-field illumination optical system adapted to condense semiconductor laser light with a wavelength of 780 to 800 nm onto the surface of the pattern formed on the object to be inspected, and conduct dark-field illumination on the pattern; a first detection optical system adapted to condense diffracted light that includes zeroth-order diffracted light entering the pupil of the objective lens after the annular diffuse illumination light converged by and irradiated from the bright-field illumination optical system has been reflected from the pattern on the object to be inspected, then receive an image of the pattern via a bright-field image sensor after the condensed light is separated into light beams having different wavelengths via a dichroic mirror, and convert the image into an image signal of the pattern; and a second detection optical system adapted to condense scattered light that is reflected from the pattern illuminated by the dark-field illumination system and enters the pupil of the objective lens, separate the condensed light into light beams having different wavelengths via a dichroic mirror, receive, via a bright-field image sensor, the light reflected from a foreign substance, and convert the received light into a signal indicative of the foreign substance; whereby the apparatus detects defect information on the pattern and information on the foreign substance.

That is, Patent Document 1 describes that the semiconductor laser light having a wavelength of 780 to 800 nm is used as dark-field illumination light, that the white light obtained using an Xe lamp and having a wavelength of 600 nm or less is used as bright-field illumination light, and that the light having a wavelength of 600-700 nm is used as illumination light for focusing. It is also described that the first detection optical system includes an attenuation filter or a phase plate at a position conjugate to the pupil of an objective lens.

Also, Japanese Laid-Open Patent Application Publication No. 2004-87820 (Patent Document 2) discloses a method and system for retrieving and referring to past inspection parameter data on similar types of semiconductor components and setting new inspection parameters.

SUMMARY OF THE INVENTION

In above Patent Document 1, however, sufficient consideration has not been paid to the selection of the optical parameters that enable the suppression of the capture rate of false defects not influencing the production yield, and highly sensitive detection of minute defects influencing the production yield and requiring detection for process monitoring, for various inspection objects on a semiconductor wafer.

In addition, in Patent Document 2, no consideration has been paid to whether a wavelength band is changed according to the kind of object to be inspected as an optical parameter.

The present invention provides a method and apparatus for optical inspection, adapted to achieve highly sensitive and rapid inspection of minute defects on a variety of inspection objects on a semiconductor wafer by suppressing the detection of false defects not influencing a production yield of semiconductor devices, and enabling high-contrast detection of minute defects influencing the production yield of the semiconductor devices and requiring detection for process-monitoring purposes.

In a method and apparatus for optical inspection, the present invention is adapted to select an appropriate illumination wavelength band in which high contrast of defects of interest can be obtained and detection of false defects can be suppressed by using an illumination optical system that can illuminate a sample with light of wide wavelength band emitted from a light source, then referring to optical parameter setup results on the same wiring material as that of a sample which has been inspected in the past.

In another method and apparatus for optical inspection, the present invention includes: a light source which emits light of plural wavelength bands; an illumination optical system which selects light of a desired wavelength band from the light of the plural wavelength bands that has been emitted from the light source, and irradiates a sample having a wiring pattern formed thereon, with the selected light; a detection optical system which receives an optical image of the sample which has been irradiated with the light of the desired wavelength band by the illumination optical system, so as to output an image signal; an image processing unit which processes the image signal which has been output from the detection optical system, so as to detect a defect; an inspection information database including, in addition to a database on an object to be inspected that is formed on the sample, a database on optical parameters (conditions) of the illumination optical system and of the detection optical system, and on image-processing parameters of the image processing unit; and input means for entering information on a material of the sample; wherein the illumination optical system includes a wavelength selector and a plurality of optical elements such as objective lenses, and wherein control means controls the wavelength selector in accordance with the wiring pattern material information of the sample that has been entered from the input means, selects, from the plurality of wavelength bands of the light which has been emitted from the light source, a wavelength band of the light with which the sample having the wiring pattern formed thereon is to be irradiated, and selects one of the plural optical elements that is appropriate for the selected light of a wavelength band.

In yet another method and apparatus for optical inspection, the present invention is adapted to include: a light source that emits light of plural wavelength bands; an illumination optical system which selects light of a desired wavelength band from the light of the plural wavelength bands that has been emitted from the light source, adjusts a polarization state of the selected light, and irradiates a sample having a wiring pattern formed thereon, with the light with polarization adjusted; a detection optical system which receives an optical image of the sample which has been irradiated with the light of the desired wavelength band by the illumination optical system so as to output an image signal; an image processing unit which processes the image signal which has been output from the detection optical system so as to detect a defect; and control unit which controls the illumination optical system to enable the light of the desired wavelength band to be selected and the polarization state of the light to be adjusted.

In yet another method and apparatus for optical inspection, the present invention is adapted to include: a light source that emits light of a wide wavelength band; an illumination optical system which irradiates an object to be inspected that is formed on a sample, with the light of the wide wavelength band that is emitted from the light source; a detection optical system includes, in addition to a wavelength separation element formed such that reflection light having the wide wavelength band from the inspection object on the sample with which the light has been irradiated by the illumination optical system is separated into reflection lights having a plurality of wavelength bands, a plurality of image sensors each of which receives optical image of each of the reflected lights separated by the wavelength separation element so as to output each of image signals; and an image processing unit which detects defects of interest; wherein the image processing unit selects a desired image signal which suppresses detection of false defects according to kind of inspection object, from the image signals obtained from the plurality of image sensors in the detection optical system, and detects the defects of interest by processing the selected image signal.

In the above illumination optical system and detection optical system of the present invention, a plurality of objective lenses whose aberration has been corrected for each of the plural wavelength bands in the wide wavelength band are each selectably disposed for common use. In the above illumination optical system, the present invention also has a bright-field illumination optical system that irradiates the sample with the light having the plurality of wavelength bands, and a dark-field illumination optical system that irradiates the sample with the light having the plurality of wavelength bands. In addition, according to the present invention, the light of the wide wavelength band that is emitted from the light source includes visible light.

Additionally, the illumination optical system in the present invention further includes a band cutoff filter group constructed such that light of a plurality of any wavelength bands can be selected from a wavelength band of visible light by combining a plurality of band cutoff filters which cut off lights of different specific wavelength bands. Furthermore, the light of the wide wavelength band that is emitted from the light source in the present invention includes visible light and ultraviolet (UV) light. The illumination optical system in the present invention further includes a band cutoff filter group constructed such that light of a plurality of any wavelength bands can be selected from wavelength bands of visible light and UV light by combining a plurality of band cutoff filters which cut off lights of different specific wavelength bands.

Furthermore, the above illumination optical system in the present invention has a wavelength selection element that switches between UV light and visible light. The above illumination optical system in the present invention further has polarizing optics capable of controlling a polarization state of the irradiated light, and the detection optical system has at least an analyzer.

The above illumination optical system in the present invention further has a polarizing control optics capable of controlling the polarization state of the irradiated light, and the detection optical system has an analyzer between the wavelength separation element and each image sensor. The detection optical system in the present invention includes a selectably disposed polarizing beam splitter, instead of the wavelength separation element.

Moreover, the above illumination optical system and detection optical system in the present invention have an objective lens for common use, and the detection optical system further has a controllable or selectable spatial filter at a position conjugate to a pupil of the objective lens.

In yet another method and apparatus for optical inspection, the present invention includes: a light source that emits light of a wide wavelength band; an illumination optical system having a wavelength selection optical element which selects light of a desired wavelength band from the light of the wide wavelength band that is emitted from the light source, the illumination optical system being adapted to irradiate a inspection object with the selected light of the desired wavelength band; a detection optical system having an image sensor which receives an optical image of reflection light having a desired wavelength band obtained from the inspection object that has been irradiated with the light, so as to output an image signal; and an image processing unit which detects defects of interest; wherein the wavelength selection optical element selects the light of the desired wavelength band which suppresses detection of false defects according to kind of the inspection object, and wherein the image processing unit detects the defects of interest by processing the image signal obtained from the image sensor in the detection optical system.

In yet another method and apparatus for optical inspection, the present invention includes: a light source which emits light of a wide wavelength band; an illumination optical system having a wavelength selection optical element which selects light having a plurality of wavelength bands from the light of the wide wavelength band that is emitted from the light source, the illumination optical system being adapted to irradiate an inspection object with light that have been selected by the wavelength selection optical element; a detection optical system including, in addition to a wavelength separation element formed such that reflected light having the plurality of wavelength bands obtained from the inspection object that has been irradiated by the illumination optical system with the light is separated into reflection lights having a plurality of wavelength bands, a plurality of image sensors which each receives optical image of each of the reflection lights that have been separated by the wavelength separation element so as to output each of image signals; and an image processing unit which detects defects of interest; wherein the image processing unit processes an image signal selected from the image signals obtained from each of the image sensors in the detection optical system so as to detect the defects of interest.

The above illumination optical system of the present invention further has a polarizing control optics capable of controlling a polarization state of the irradiated light, and the detection optical system has a analyzer between the wavelength separation element and each image sensor.

In yet another method and apparatus for optical inspection, the present invention includes: a light source which emits light having a wide wavelength band; an illumination optical system having a wavelength selection optical element which selects light having a plurality of wavelength bands from the light of the wide wavelength band that is emitted from the light source, the illumination optical system being adapted to irradiate an inspection object with the light that has been selected by the wavelength selection optical element; a detection optical system including, in addition to a polarizing separation element formed such that reflection light having the plurality of wavelength bands obtained from the inspection object that has been irradiated by the illumination optical system is separated into reflection lights having different polarization states, a plurality of image sensors which each receives optical image of each of the reflection lights that have been separated by the polarizing separation element so as to output each of image signals; and an image processing unit which detects defects of interest; wherein at least the illumination optical system or the detection optical system further has a polarizing control optics capable of controlling polarization states, the wavelength selection optical element of the illumination optical system is adapted such that the wavelength selection optical element selects the light of the desired wavelength band which suppresses detection of false defects according to kind of the inspection object, and the image processing unit detects the defects of interest by processing an image signal selected from the image signals obtained from each of the image sensors in the detection optical system.

These and other objects, features, and advantages of the invention will be apparent from the following more particular description of preferred embodiments of the invention, as illustrated in the accompanying drawings.

DESCRIPTION OF THE PREFERRED EMBODIMENTS

Embodiments of a method and apparatus for inspecting defects according to the present invention will be described hereunder using the accompanying drawings.

In a method and apparatus for inspecting defects according to the present invention, a detection ratio of false defects to be excluded from detection during defect inspection of various inspection targets (elements or objects to be inspected) that are present on semiconductor wafers, is reduced below a reference value. The inspection targets here are, for example, gates, bit lines (made of Al or the like), metallic electrical interconnects or wiring (made of TiN/Al/TiC, Cu, or the like), device isolators or trench isolators (made of Si and $SiO_2$), and the like. At the same time, defects that need to be detected since they affect a production yield of the semiconductor wafers (these defects to be detected include defects of interest, or DOI), and defects that need to be detected for process-monitoring purposes are also made detectible at high contrast. Highly sensitive and rapid inspection of defects is thus implemented. The false defects to be excluded from detection appear brightness differences of detected images according to particular differences in dielectric film thickness and grain etc. on the semiconductor wafer as a large difference image (a large brightness difference) when light of a narrow-band wavelength is irradiated and for example images of dies formed with the same pattern for design-related reasons or purposes are compared. These false defects are originally to be excluded from detection since they usually have no adverse effects on electrical characteristics of semiconductor devices. For the inspection targets on the semiconductor wafers, therefore, it is necessary that the detection ratio of false defects be reduced below a reference value, with highly sensitive detection of the defects of interest (DOI).

First Embodiment

A first embodiment of an optical defect inspection apparatus according to the present invention will be described hereunder.

Figure 9:
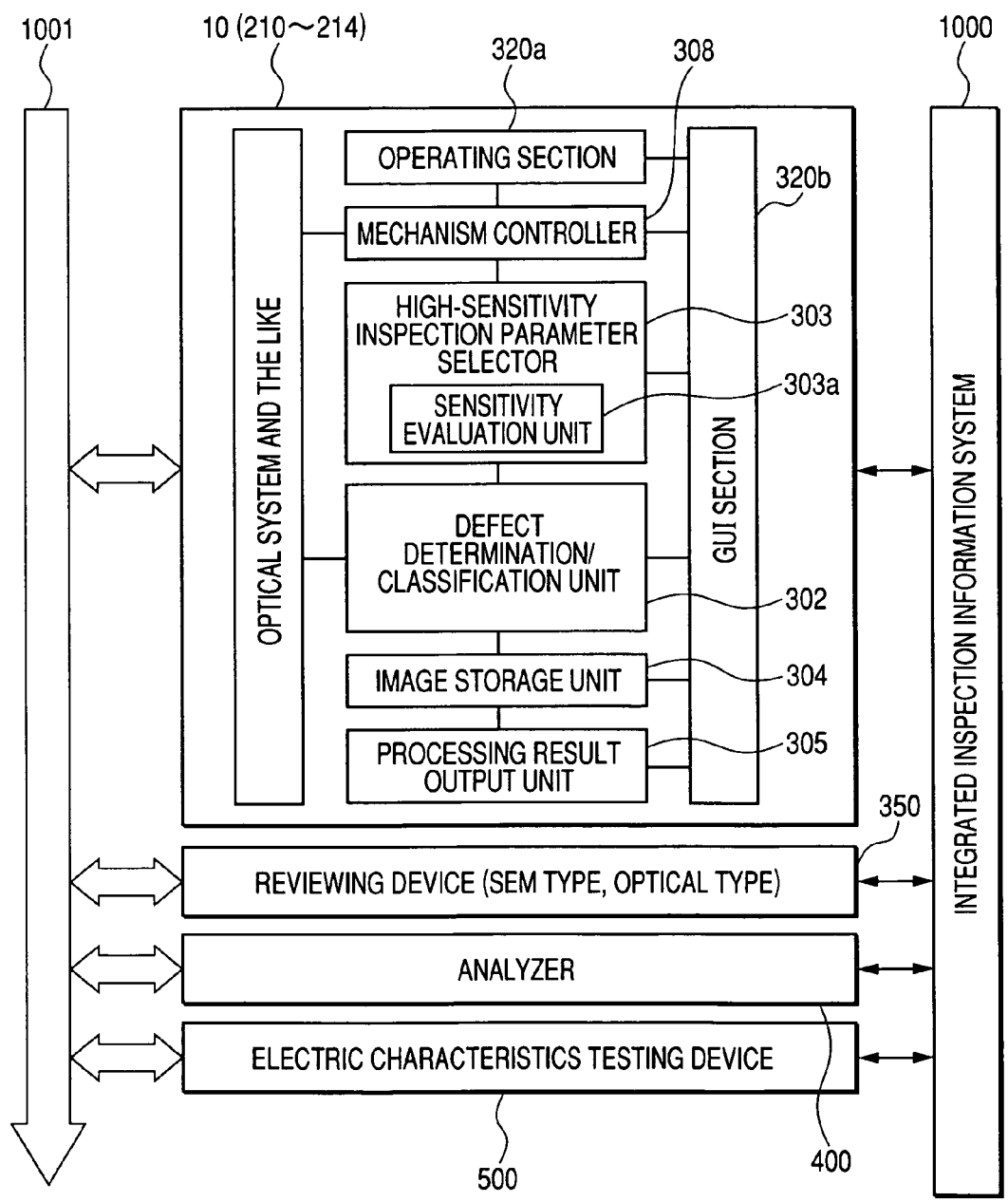
FIG. 9 is a diagram showing an entire system configuration according to an embodiment of the present invention.

First, an entire system according to the present invention is described below using FIG. 9. An optical defect inspection apparatus 1 of the present invention, a reviewing device (SEM type, optical type) 350, an analyzer (FIB processing device, a sectional SEM reviewing device) 400, and an electric characteristics testing device (a tester) 500 are connected to an integrated inspection information system (host system) 1000 through a network. The optical defect inspection apparatus 1 has an optical system 10a that includes stages 210 to 214, an operating unit 320 that includes an operating section 320a and a GUI unit 320b, a mechanism controller 308 that controls all internal mechanisms of an optical system 10, inclusive of the stages, and an image processing unit 300. The image processing unit 300 includes: a high-sensitivity inspection parameter selector 303 that functionally includes a sensitivity evaluation unit 303a and selects high-sensitivity inspection parameters (conditions), such as optimum optical parameters and determination process parameters, according to the kind of object to be inspected; a defect determination/ classification unit 302 that determine/classify defects based on images acquired by the optical system 10a and/or the like; an image storage unit 304 that stores the images and the like that have been subjected to the determination/classification; and a processing result output unit 305.

Figure 1:
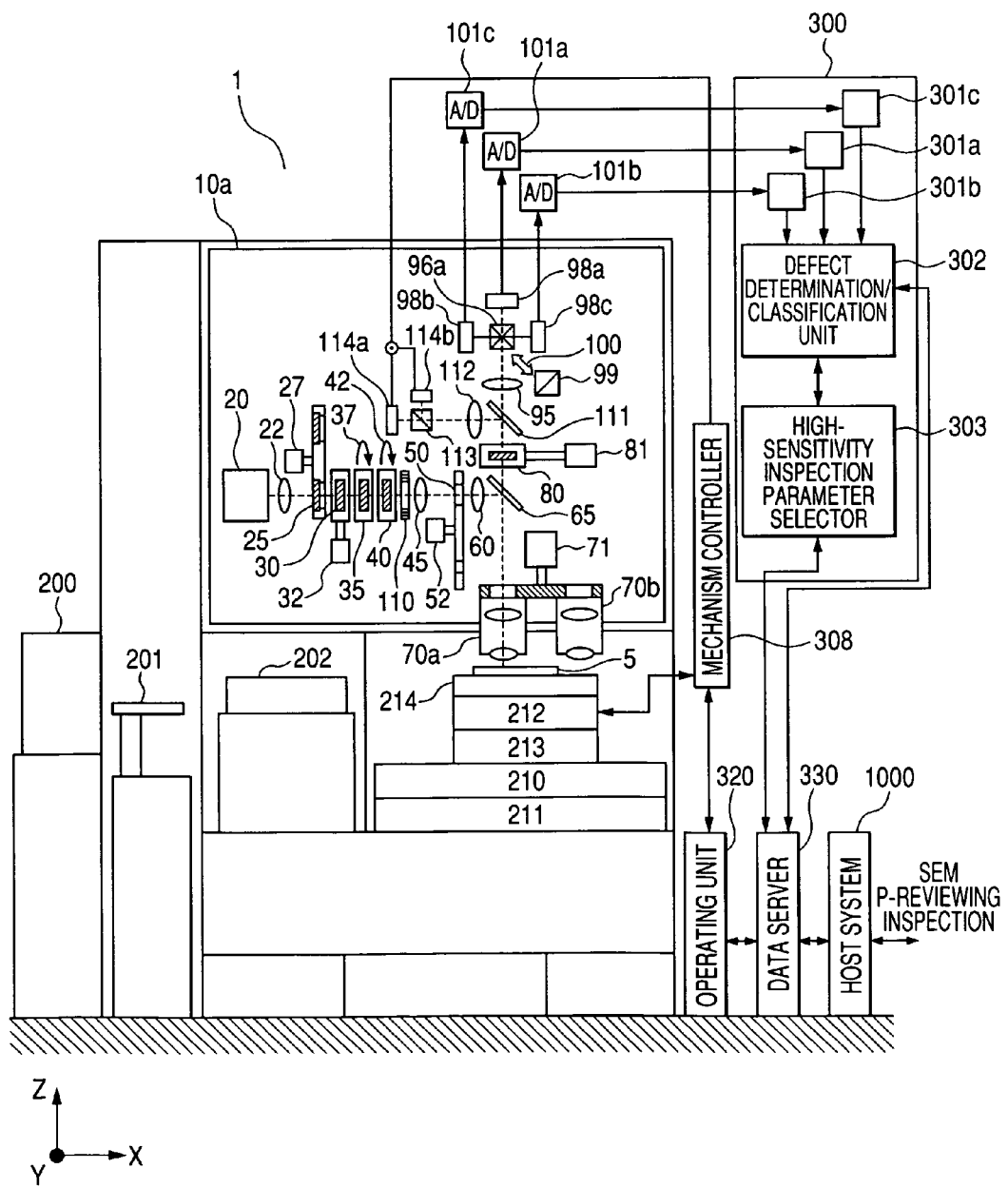
FIG. 1 is a front view showing a basic configuration of an optical inspection apparatus according to a first embodiment of the present invention.

Next, a basic configuration of the optical defect inspection apparatus 1 according to the present invention is described using FIG. 1. A wafer 5 stored within a hoop 200 is carried into a θ-aligner 202. The wafer 5 is pre-aligned by the θ-aligner 202. After the pre-alignment, the wafer 5 is vacuum-chucked by a wafer chuck 214 mounted on a stage section consisting of an X-stage 210, a Y-stage 211, a Z-stage 212, and a θ-stage 213. The optical system 10a that detects an image of the wafer surface is disposed above the wafer 5 (a configuration of a bright-field illumination optical system based on fall-illumination is shown in FIG. 1).

This bright-field illumination optical system includes a light source 20, a lens 22, a wavelength selection filter 25, a polarizer 30, a half-wave plate 35, a quarter-wave plate 40, a lens 45, aperture stops 50, a lens 60, a beam splitter 65, and objective lenses 70a, 70b.

A detection optical system includes the objective lenses 70a, 70b, the beam splitter 65, an analyzer 80, an imaging lens 95, a wavelength separation filter (dichroic mirror) 96a, and image sensors 98a-98c.

A focused focal point detecting system includes a striped pattern 110 disposed in the illumination system, a lens 112, a beam splitter 113, and focus detection image sensors 114a, 114b.

The light source 20 emits light of a wideband wavelength (e.g., about 350 to 700 nm in a range from UV light to visible light), and the light source 20 is, for example, a xenon (Xe) lamp, an ultrahigh-pressure mercury (Hg) lamp, an Hg—Xe lamp, a halogen lamp, or the like. Light from the light source is passed through the lens 22, the wavelength selection filter 25, and the polarizer 30, in that order. The wavelength selection filter 25 is formed of, for example, an interference filter or a colored glass member having an absorption band at a specific wavelength. Multiple kinds of filters different in transmission wavelength constitute the wavelength selection filter 25. The multiple kinds of filters are arranged to a wavelength selection filter switcher 27 controlled by a mechanism controller 308 and including a motor and other elements, and these filters make illumination wavelength switching possible. That is to say, the wavelength selection filter 25 selects at least UV light having a wavelength of about 350 to 450 nm (purple band included), and visible light with a wavelength of about 400 to 700 nm. It is possible to select UV light by using a visible-light cutoff filter that shields light of about 450 nm or more. It is possible to select visible light by using a UV-light cutoff filter that shields light of about 350 to 400 nm.

If the light source 20 emits only visible light of about 400 to 700 nm to detect reflection, diffraction, or scattering of the visible light obtained from a pattern on the object under inspection, the wavelength selection filter is, of course, not always required. This is because, as described later herein, the visible light can be detected by separating the light into light beams with different wavelengths via the wavelength separation filter (dichroic mirror) 96a of the detection system.

The polarizer 30 is disposed to improve defect image contrast (difference in grayscale level) by polarization illumination. After being passed through the polarizer 30, light becomes linearly polarized light and penetrates through the half-wave plate 35 that rotates an azimuth of an oscillation direction of the light. In accordance with a direction of the wiring pattern, the light that has penetrated through the half-wave plate 35 is controlled to obtain an oscillation direction for improved defect image contrast. The half-wave plate 35 is mounted on a half-wave plate rotator 37 adapted for rotating the oscillation direction of the above-penetrated light in an arbitrary direction. For improved capture rates of diverse kinds of defects, the quarter-wave plate 40 for elliptical polarization illumination is also disposed since elliptical polarization illumination (inclusive of circularly polarized light illumination with an ellipticity of 1) may be effective. The quarter-wave plate 40 is mounted on a quarter-wave plate rotator 42 adapted for changing an elliptic shape of penetrated light to any other shape. The polarizer 30 is unnecessary when sufficient sensitivity is obtainable without polarization illumination. In order to minimize a loss of illumination light due to the polarizer 30, therefore, the polarizer is installed in a polarizer extending/retracting mechanism 32 for removing the polarizer from an illumination optical path. The half-wave plate 35 and the quarter-wave plate 40 are unnecessary for random polarization illumination. However, if these wave plates are made of, for example, a crystal, magnesium fluoride, or the like, sine transmittance of at least 90% can be obtained, the amount of light lost will be of a negligible level, even when the wave plate remains disposed. Accordingly, the half-wave plate 35 and the quarter-wave plate 40 may be disposed on the optical path or removed therefrom, even for random illumination. The polarizer extending/retracting mechanism 32, the half-wave plate rotator 37, and the quarter-wave plate rotator 42 are controlled under control commands from the mechanism controller 308.

After being passed through these optical elements, light travels through the lens 45 and reaches the aperture stops 50, where an image of the light source is then formed. The light is further passed through the aperture stops 50 and the lens 60 and then reflected from the beam splitter 65. Thus, the light illuminates the wafer 5 via the objective lenses 70a, 70b by fall-illumination (bright field illumination). The multiple kinds of aperture stops 50 each different in aperture shape and in stop diameter are arranged on an aperture stop switcher 52 controlled by the mechanism controller 308 and including a motor and other elements. The shapes of the aperture stops 50 include, for example, a circular shape formed around an optical axis, an annular aperture shape with a ring-shaped aperture outside the optical axis, and bipolar or quadrupolar aperture shapes with an aperture outside the optical axis. The aperture stop switcher 52 is operated so that an aperture stop shape effective for improving defect image contrast and reducing nuisance (false defect) image contrast is selected (as a parameter of illumination s) on an optical path from the multiple kinds of aperture stops. An image of the thus-selected aperture stop 50 is projected onto a pupil of the objective lens 70a, 70b, resulting in Koehler illumination.

When the visible light ranging from about 400 to 700 nm in wavelength is selected by the wavelength selection filter 25 of the illumination optical system and the objective lens 70a for visible light serves as Koehler illumination, the light is reflected, diffracted, or scattered from the pattern or some other object on the wafer 5. Among the reflected, diffracted, or scattered lights, only a light that travels in the range of the NA (Numeral Aperture) of the objective lens 70a is recaptured by the lens 70a. Also, light that has been passed through the beam splitter 65 is further passed through the analyzer 80 that transmits only oscillation components of a specific electric-field vector, and then imaged by the imaging lens 95. After this, the wavelength separation filter (dichroic mirror) 96a separates the light into, for example, three wavelength bands (e.g., a green band of about 500 to 600 nm, a red band of about 600 to 700 nm, and a blue band of about 400 to 500 nm). Those images of the pattern on the wafer 5 which are associated with the light of the three wavelength bands, for example, are formed on the image sensors (e.g., TDI sensors) 98a to 98c, respectively. Thus, the light can be received by these image sensors. In other words, since the wavelength selection filter 25 in the illumination system has selected the visible light having a wavelength of about 400 to 700 nm, the wavelength separation filter (dichroic mirror) 96a in the detection system can separate the light into three wavelength bands by, for instance, reflecting the light with the red band of about 600 to 700 nm, reflecting the light with the green band of about 500 to 600 nm, and transmitting the remaining light with the blue band of about 400 to 500 nm. The light of the red band that has been obtained from the separation by the above reflection is received by the image sensor 98b, the light of the green band that has been obtained from the separation by the above reflection is received by the image sensor 98c, and the light of the blue band that has been obtained from the separation by the above transmission is received by the image sensor 98a. Image signals associated with each wavelength band are then output.

Alternately, the wavelength separation filter 96a in the detection system can, of course, separate light into three wavelength bands by reflecting the light with the red band of about 600 to 700 nm, reflecting the light with the blue band of about 400 to 500 nm, and transmitting the remaining light with the green band of about 500 to 600 nm. In this latter case, the wavelength bands of the light received by the image sensors 98a to 98c differ from the wavelength bands of the light received in the former case.

If the object to be inspected is a gate, therefore, since defects obtained using light with a wavelength band of about 400 to 450 nm look bright, the image signal obtained from the image sensor 98a can be used to detect the defects accurately because of improved resolution. An aluminum (Al) wiring pattern may have a TiN film stacked on the surface, and, if so, the TiN film has the characteristics that its reflectivity tends to rise at a wavelength band of 450 to 500 nm. Accordingly, depending on a relationship between a reflectivity of the pattern and that of its background (underlayer), the wavelength at which the DOI can be detected with a high contrast varies, such as below 450 nm or above 500 nm. If the object to be inspected is metal wiring (or the like) made of copper (Cu), since defects obtained using light with a wavelength band of about 550 to 700 nm look bright, the image signal obtained from the image sensor 98b can also be used to detect the defects accurately because of improved resolution. If the object to be inspected is a device isolator, since this isolator is formed of Si and $SiO_2$, the isolator has no dependence upon wavelength and thus the image signal obtained from any one of the image sensors 98a to 98c can be used to bring out latent or obscure defects more clearly to a detectable level equivalent to the above. If a wavelength side shorter than and a wavelength side longer than the wavelength at which optical constants (n, k) vary are both made usable for illumination in the above manner with spectral optical constants of the semiconductor material being taken into consideration, this is effective for extensive, highly sensitive inspection of the wafers manufactured through various processes and having different structures. In other words, it is effective to split light into a wavelength band of UV light, a blue band of visible light, a green band of visible light, and a red band of visible light, since it is possible to substantially cover the spectral constants of the material used in a semiconductor, and the short-wavelength side and long-wavelength side of change points of spectral reflectivities.

As described later herein, therefore, during routine inspection, the high-sensitivity inspection parameter selector 303 can establish parameters (conditions), that is, select whether, based on the kind of object to be inspected, the image processing unit 300 is to perform the defect determination using the image signal obtained from any one of the image sensors 98a to 98c. The image sensors receive the light of the wavelength band in which high-contrast image signals will be obtained for DOI. For a specific kind of object to be inspected, it is possible to use an image signal of the wavelength band of about 500 to 700 nm, for example, during defect determination, by converting, from analog to digital, the image signals obtained from the image sensors 98b and 98c, for example, and then synthesizing the converted signals.

When UV light of about 350 to 450 nm (inclusive of purple) is selected via the wavelength selection filter 25 of the illumination system and the UV light objective lens switched under control of the mechanism controller 308 serves as Koehler illumination, a light traveling in the range of the NA (Numeral Aperture) of the objective lens 70b among lights that have been reflected, diffracted, or scattered from the pattern or the like on the wafer 5 is recaptured by the objective lens 70b. In addition, light that has been passed through the beam splitter 65 is further passed through the analyzer 80 that transmits only oscillation components of a specific electric-field vector, and then imaged by the imaging lens 95. After being further passed through the wavelength separation filter (dichroic mirror) 96a, the light forms an image of the pattern of the wafer 5 on the image sensor (e.g., TDI sensor) 98a and is received by this sensor. The image sensor 98a, therefore, needs to have sensitivity to UV light.

Since the analyzer 80 is not used similarly to the illumination system in some cases, the analyzer 80 is constructed so that an extending/retracting mechanism 81 can extend and retract the analyzer with respect to the optical path.

Figure 2:
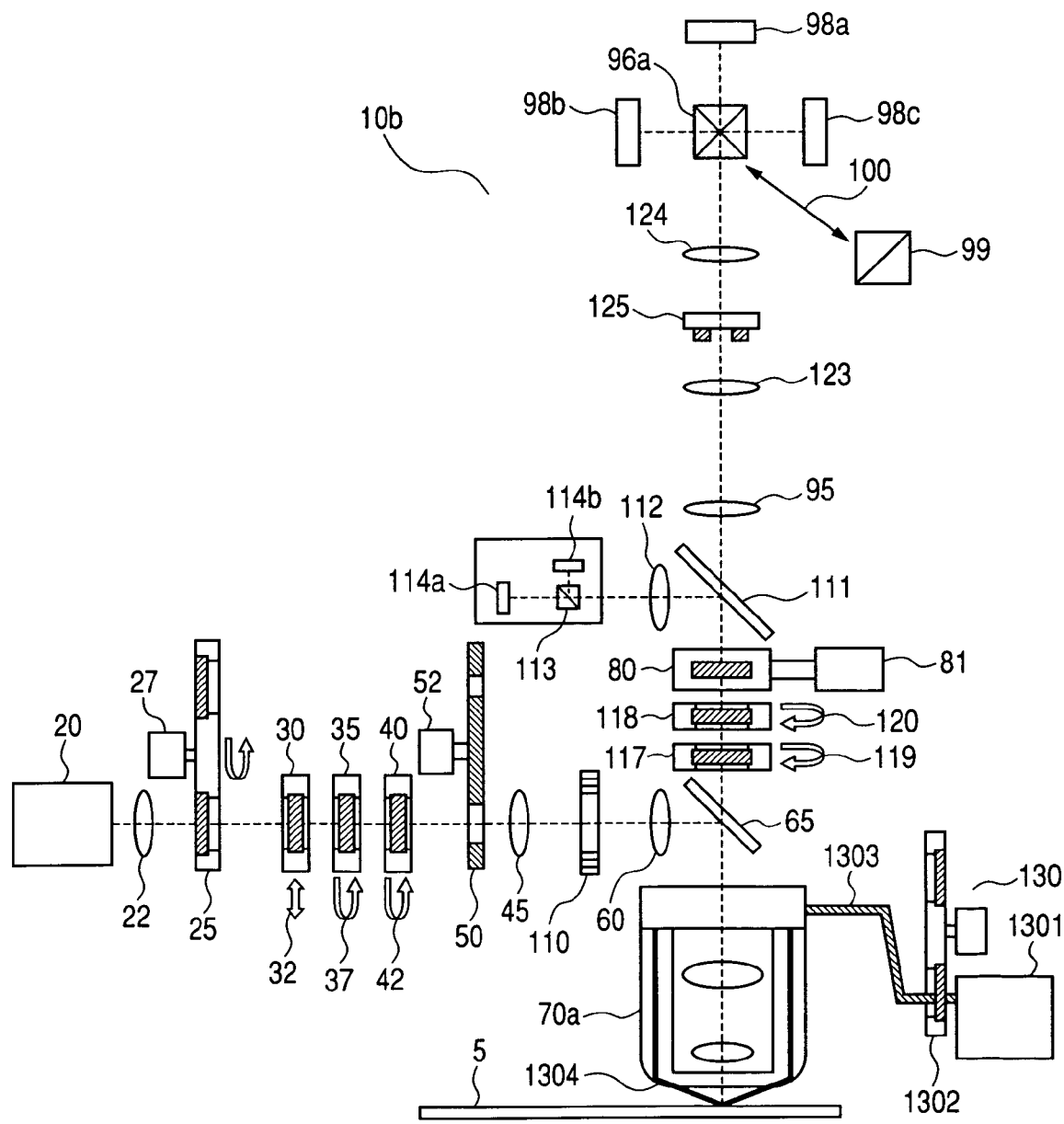
FIG. 2 is a front view showing an optical system configuration of an optical inspection apparatus according to a second embodiment of the present invention.

The apparatus also has a polarizing beam splitter 99 that splits light into, for example, P-polarized light and S-polarized light and that is adapted to be made selectable via a switcher 100 under the control of the mechanism controller 308, instead of the wavelength separation filter 96a. That is to say, the wavelength separation filter 96a and the polarizing beam splitter 99 can be switched using the switcher 100. In particular, if the object to be inspected has little dependence upon a wavelength of visible light (white light) and the pattern on the object has directionality, images of the split polarized-light components, for example, of the pattern on the wafer 5 can be formed on the image sensors (e.g., TDI sensors) 98a, 98b, by switching control from the wavelength separation filter 96a to the polarizing beam splitter 99. An optical image that identifiably represents defects can also be received using either of the image sensors. Additionally, as shown in FIG. 2, a spatial filter 125 constituted by multiple kinds of phase difference filters may be switchably installed at a position conjugate to the pupil of the objective lens 70a, 70b, on the optical path. Since the pupil of the objective lens 70a and that of the objective lens 70b change in position, the conjugate installation position for the spatial filter 125 also changes accordingly. Installing the spatial filter requires collimator lenses 123, 124. Alternatively, the spatial filter 125 may likewise be constructed by using multiple kinds of transmittance filters capable of being changed over from one kind of filter to another.

The NAs and imaging magnifications of the objective lenses need to be changed based on the wavelength of the light emitted. Therefore, the apparatus includes, for example, the visible-light objective lens 70a that has been aberration-corrected with visible light, and the UV-light objective lens 70b that has been aberration-corrected with UV light (may include short-wave band components of visible light). These objective lenses are constructed so that either can be selected via a revolver (switcher) 71 under the control of the mechanism controller 308. In this manner, the objective lenses 70 can be changed according to the particular wavelength of the illumination light, a selected inspection rate, or the contrast of the defect image. As a result, the NAs and imaging magnifications of the objective lenses can also be changed to conduct inspections appropriate for an inspection recipe. In the above cases, it is difficult to design and manufacture the optical system that realizes chromatic aberration correction of various kinds of light up to DUV (Deep Ultraviolet) light or up to UV light or visible light, since the kinds of glass materials that can be used are limited. The objective lenses 70, in particular, require advanced processing technology and are difficult to simultaneously satisfy three requirements, namely, a broadband wavelength, a high NA (Numerical Aperture), and a wide field. For these reasons, the above multiple objective lenses are employed and these lenses are constructed so that either can be selected according to the wavelength band used.

As described above, according to the first embodiment, it is possible to use, for example, four wavelength bands, namely, a red band of about 600 to 700 nm, a blue band of about 400 to 500 nm, a green band of about 500 to 600 nm, and a UV band, to be suitable for an object to be inspected. It is also possible to select, for example, a polarization azimuth based on control of polarization, and a phase difference based on spatial filtering to be suitable for an object to be inspected.

In addition, a beam splitter 111 is disposed on the optical path, and light that has been reflected by the beam splitter 111 becomes focus position detection light for detecting an optical misalignment level of a focal position of the objective lenses 70a, 70b with respect to the surface of the wafer 5. During focus detection, by way of example, the striped pattern 110 disposed in the illumination system is projected onto a peripheral portion of a detection field on the wafer 5 and the resulting image is guided to a focus detection system 112 to 114. Two focus detection image sensors, 114a, 114b, are arranged at positions where are defocused at the wafer side and the opposite side with respect to an imaging position (a designed image surface) of the striped pattern when the surface of the wafer 5 is at a focused focal point. Reference number 113 denotes a beam splitter (half-mirror) that branches the optical image of the striped pattern, obtained from the surface of the wafer 5. The mechanism controller 308 compares contrasts of the optical images of the striped pattern obtained from the detection by the image sensors 114a, 114b, and detects a positional relationship between the surface of the wafer 5 and the focused focal point. If the surface of the wafer 5 is optically shifted against the focused focal point, the mechanism controller 308 instructs the Z-stage 212 to move according to the amount of particular displacement. Thus, the surface of the wafer 5 is controlled to match to the focused focal point. In recipe contents confirmation S112 of FIG. 11, if, as shown in item (2) of FIG. 11, a focus-matching layer is an underlayer to be inspected (if the layer on which the pattern is formed is shifted with respect to the surface), there is a need to conduct focus matching by calculating focus offset data.

The image sensors 98a to 98c are, for example, linear image sensors (including a TDI: Time Delay Integration type), and these image sensors continuously detect an image of the wafer 5 while moving the X-stage 210 at a constant speed. Image information from the image sensors 98a to 98c is converted into digital signal image form by A/D converters 101a to 101c and then input to image preprocessors 301a to 301c of the image processing unit 300.

The image preprocessors 301a to 301c of the image processing unit 300 correct image nonuniformity according to particular illuminance distribution in the field and uniformity of the sensor sensitivity. The corrections include nonlinear image brightness conversion such as gamma correction of the image. The defect determination/classification unit 302 first compares between the images formed with the same pattern for design reasons or purposes, the images being obtained from the image preprocessors 301a-301c beforehand, and determines defect candidates. Die comparison for comparing between images of adjacent dies, and cell comparison for comparing between images of adjacent memory cells are typical examples of image comparison schemes. There is also a technique for determining defect candidates by comparing design pattern data with an image that the image sensor 98 has detected, or by comparing a reference image generated from images of multiple dies with an image detected by the image sensor 98. Information on defect portions (including defect candidates) for which defect judgments have been conducted by the defect determination/classification unit 302 includes, for example, a detection image of each defect portion, an image used as a reference image for comparison with the detection image, and/or a differential image (brightness difference) of compared the detection image with the reference image. The above information also includes position coordinate information of the defect portion, and image feature quantitieces (brightness difference (contrast), area, and length (projection length)) of the defect portion that have been calculated for defect determination. The above various types of information are stored into the inspection information databases (DBs) 3301 of a data server 330, shown in FIG. 10. Wafer information (process, product type, lot number, and more), the image that has been determined as a defect portion (defect candidates included), that is, the detection image of the defect candidates or of the defect portion, the reference image used as a basis for comparison, and/or the differential image (brightness difference) of compared the detection image with the reference image are stored into an inspection target DB of the inspection information DBs 3301. The position coordinate information of the defect portion, and the image feature quantities thereof are also stored into the inspection target DB. These diverse sets of information can be displayed using the operating unit 320. The operating section 320a in the operating unit 320 of the entire inspection apparatus issues a variety of instructions for, for example, the loading of the wafer 5, θ-alignment of the wafer, high-sensitivity inspection parameter selection (setting up a plurality of optical parameters (conditions), and parameter setup test inspection), the process steps shown in FIG. 12, such as a preliminary test inspection step (S122), inspection parameter selection step (S126), and test inspection step (S127), and execution of routine inspection. If an inspection recipe is already created for the wafer 5, wafer inspection automatically starts and other operations can be controlled from outside in accordance with the instructions given from the host system 1000 which can communicate with the inspection apparatus 1. Inspection result information can also be searched, extracted, and displayed from the host system 1000. A system is provided that even if an operator issues an instruction from a main unit of the inspection apparatus 1, inspection results can be confirmed from an outside region (e.g., the outside of a clean room).

Figure 10:
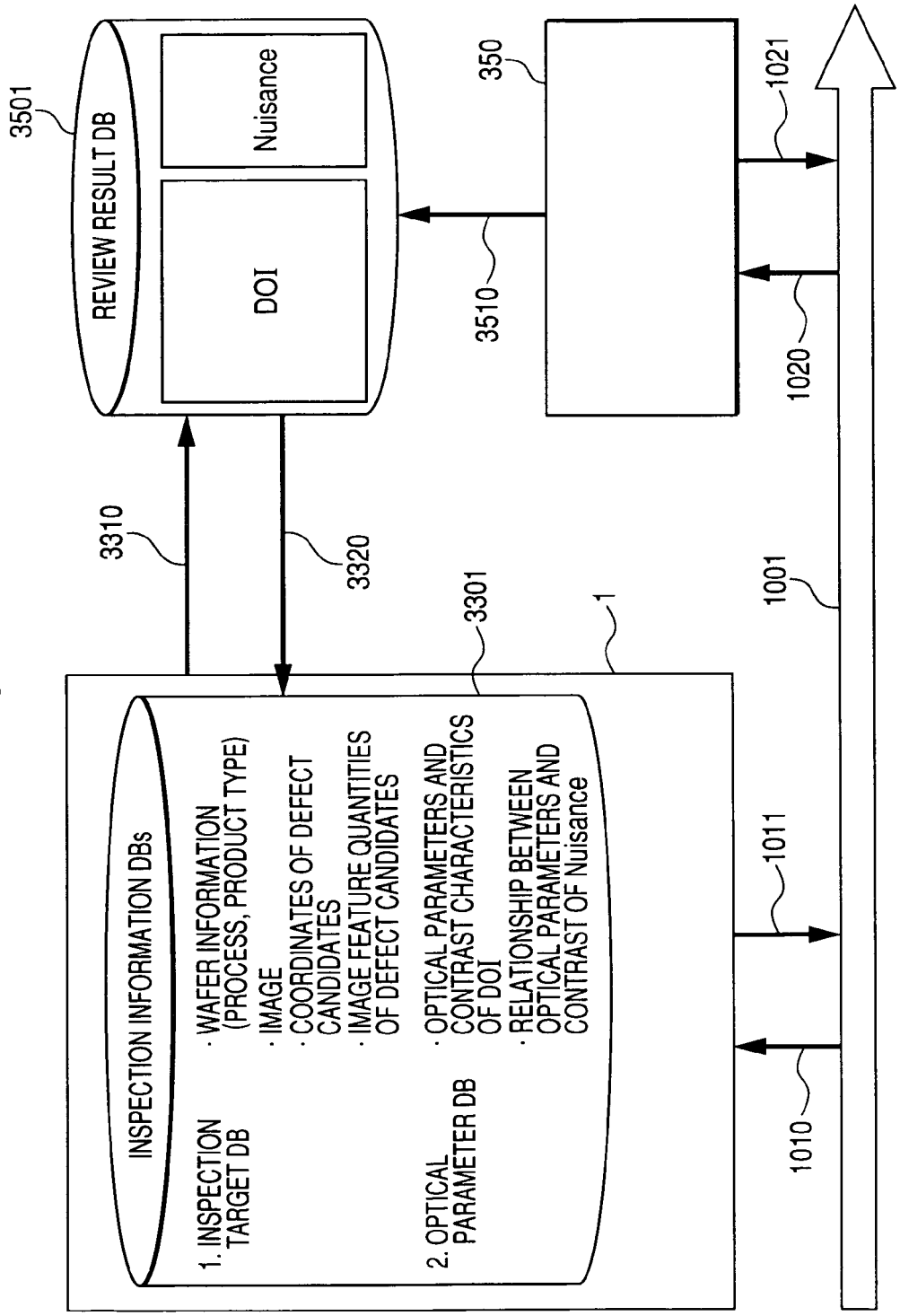
FIG. 10 is a diagram showing a relationship between an inspection information database (DB) of an optical inspection apparatus and a review result database (DB) of a reviewing device, for the preliminary test inspection and test inspection that use a sample for parameter setup in the present invention.

Additionally, position information on the position coordinates on the wafer and other factors of the defect portion (defect candidates included), image information on the detect portion, and other information are supplied from the host system 1000 to devices such as the reviewing SEM device 350 and a probe testing device (an electric characteristics testing device) 500. As shown in FIG. 10, therefore, the reviewing SEM device 350 conducts reviews based on the defect candidate information, and classifies defect candidates into the defects of interest (DOIs) that affect the yield and false defects (nuisance) that do not affect the yield. After the classification, SEM images of each DOI and nuisance are acquired as ADR (Automatic Defect Review) images and then stored into a review result DB 3501 through a constituent element 3510. Consequently, review results are supplied from the review result DB 3501 of the reviewing SEM device 350 through a constituent element 3320 to an optical parameter (condition) DB within the inspection information DBs 3301 of the inspection apparatus 1.

As set forth above, according to the first embodiment, since inspection parameters for high-contrast detection of the defects of interest can be set up according to the object to be inspected, a detection ratio of the false defects originally to be excluded from detection can be reduced to or below a reference value. Thus, only the defects of interest can be detected at high sensitivity.

During routine inspection, the defect determination/classification unit 302 also classifies defects into pattern defects, foreign substance (particle), scratch defects, or others based on the image feature quantities of each defect candidate (defect portion) that have been calculated based on optical inspection parameters (the wavelength bands, polarization azimuths, phase differences, and other optical inspection parameters) that have been selected according to the object to be inspected, and on determination process parameters (determination threshold levels with respect to brightness differences (contrast) on the basis of the detection ratio of false defects (nuisance)). Routine inspection result information is stored into the data server 330. The information can be displayed and output to the GUI section 320b of the operating unit 320. The information can also be supplied to the integrated inspection information system (host system) 100 and the like.

Second Embodiment

A second embodiment according to the present invention differs from the first embodiment in terms of configuration of an optical system 10b, as shown in FIG. 2. The optical system 10b differs from that in the first embodiment in the following aspects. First, a half-wave plate 117 and a quarter-wave plate 118, both for controlling the polarization azimuth of the reflected light obtained from the wafer 5, are disposed between the beam splitter 65 and the analyzer 80 installed on a rotatable mechanism 81, on a detection optical path. Secondly, collimator lenses 123, 124, and a spatial filter 125 constituted by phase difference filters are arranged at positions conjugate to the pupil of the objective lens 70a, between the imaging lens 95 and the wavelength separation filter (dichroic mirror) 96a. Thirdly, the optical system 10b includes a dark-field illumination optical system (oblique illumination optical system) 130. The dark-field illumination optical system 130 is constituted by sections such as: a lamp light source 1301 constructed from, for example, an Hg—Xe lamp (or the like) that emits light of a broadband wavelength so as to achieve dark-field illumination of an illumination scheme; a wavelength selection filter 1302 that selects, for example, UV light and visible light from the light of a wide band, emitted from the lamp light source; an optical fiber 1303 through which the beams selected by the wavelength selection filter 1302 are guided to, for example, surrounding regions of the objective lens 70a for visible light; and a parabolic mirror 1304 by which the light reflected and directed downward from an upper-end surrounding section of the objective lens will be re-reflected to irradiate the wafer 5 from an oblique direction.

Objective lens 70b for UV light is omitted from FIG. 2.

Constructing the optical system 10b in this way enables the inspections under dark-field illumination (oblique illumination) to be conducted similarly to the inspections under bright-field illumination. That is to say, light that has been passed through the beam splitter 65 is further passed through the analyzer 80 that transmits only oscillation components of a specific electric-field vector, and then imaged by the imaging lens 95. After this, the wavelength separation filter (dichroic mirror) 96a separates the light into, for example, three wavelength bands (e.g., a green band of about 500 to 600 nm, a red band of about 600 to 700 nm, and a blue band of about 400 to 500 nm). Those images of the pattern on the wafer 5 which are associated with the light of the three wavelength bands, for example, are formed on the image sensors (e.g., TDI sensors) 98a to 98c, respectively. Thus, the light can be received by these image sensors. At the same time, rotation control of both a half-wave plate rotator 119 and a quarter-wave plate rotator 120 enables the image sensors 98a to 98c to receive the light by adapting the polarization azimuth (oscillating direction of the electric-field vector) to the pattern formed on the object under inspection. The same also applies when the polarizing beam splitter 99 is selected instead of the wavelength separation filter 96a. As can be understood from the above, the polarized light components obtained from the pattern can be erased and the defects of interest can be detected at high contrast during dark-field illumination, by controlling the polarization azimuth similarly to bright-field illumination.

In addition, since minute depressions and projections (microscopic asperities) usually exist on the surface of the object under inspection, changing over the spatial filter 25 consisting of the appropriate phase difference filters makes it possible to increase or reduce interference strength and detect the defects of interest at even higher contrast with minimum effects of the underlayer and surroundings.

As described above, according to the second embodiment, the dark-field illumination scheme effective for detecting the defects having a stepped or rough surface, such as foreign substance and scratches, can be selected in addition to the bright-field illumination scheme of the first embodiment that is convenient for detecting low-stepped remainders of thin films, minute electrical shorting defects, defects in the shape of the pattern, and other defects.

The second embodiment also makes it possible to combine dark-field illumination and bright-field illumination, and to reduce the contrast of the grains occurring on the surface of a metallic wiring pattern (e.g., aluminum wiring). The second embodiment is therefore effective for improving inspection sensitivity by reducing defect determination threshold levels.

Third Embodiment

Figure 3:
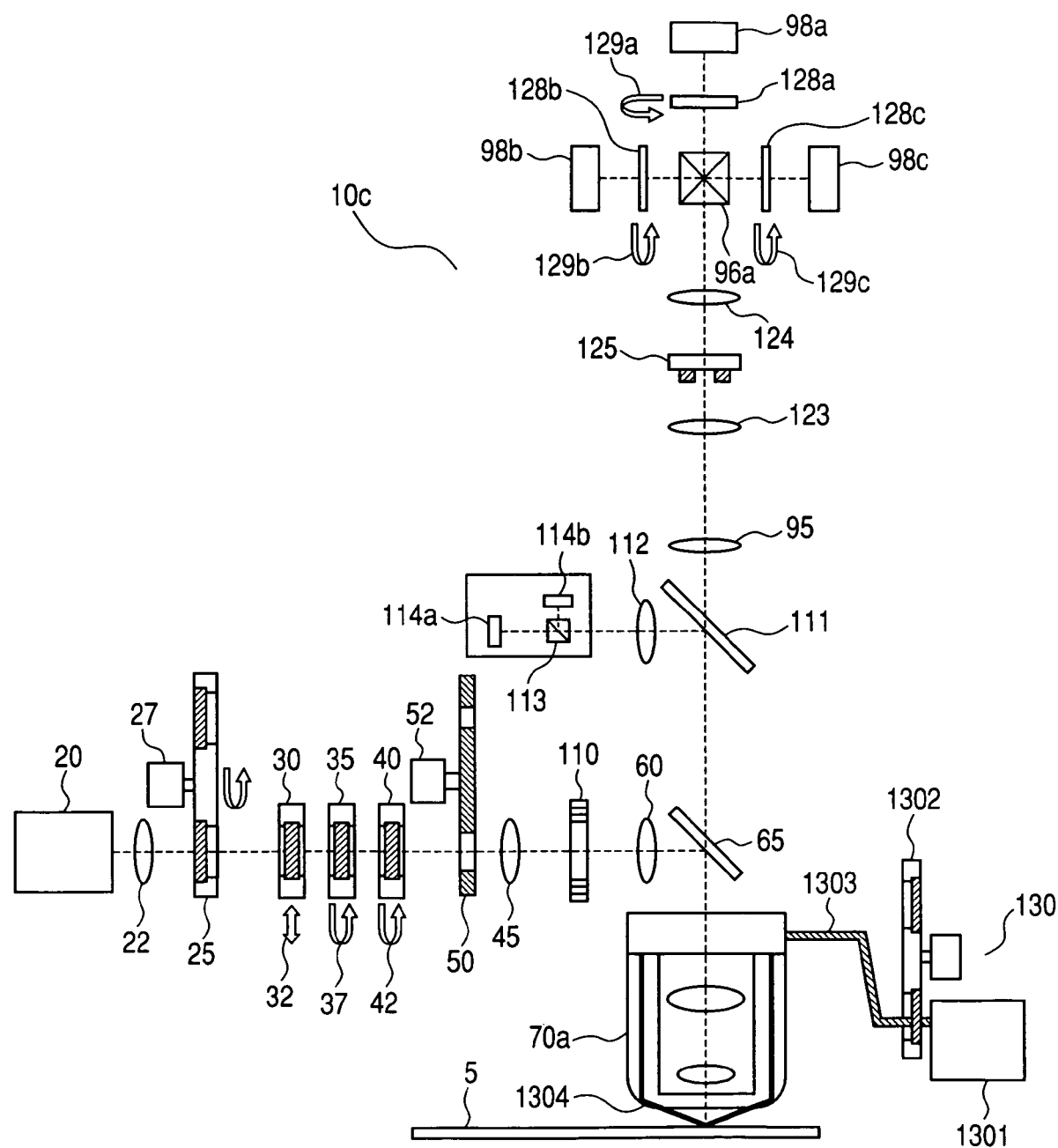
FIG. 3 is a front view showing an optical system configuration of an optical inspection apparatus according to a third embodiment of the present invention.

A third embodiment according to the present invention differs from the second embodiment in terms of configuration of an optical system 10c, as shown in FIG. 3. The optical system 10c differs from that in the second embodiment in that the half-wave plate 117, half-wave plate 119, quarter-wave plate 118, and quarter-wave plate 120 used in the second embodiment are replaced by analyzers 128a to 128c arranged between the wavelength separation filter (dichroic mirror) 96a and each of the image sensors 98a to 98c. Consequently, the polarized light components obtained from the pattern on the object to be inspected can be erased and the defects of interest can be detected at high contrast during dark-field illumination. More specifically, these can be accomplished by conducting independent adjustments on polarization azimuths (oscillating directions of electric-field vectors) of the analyzers 128a to 128c in each of three split wavelength bands, for example, via rotation controllers 129a to 129c so as to support patterns similarly to bright-field illumination.

As described above, according to the third embodiment, polarization azimuths can be adjusted so as to support patterns in each of the three split wavelength bands, for example, during bright-field illumination.

Fourth Embodiment

Figure 4:
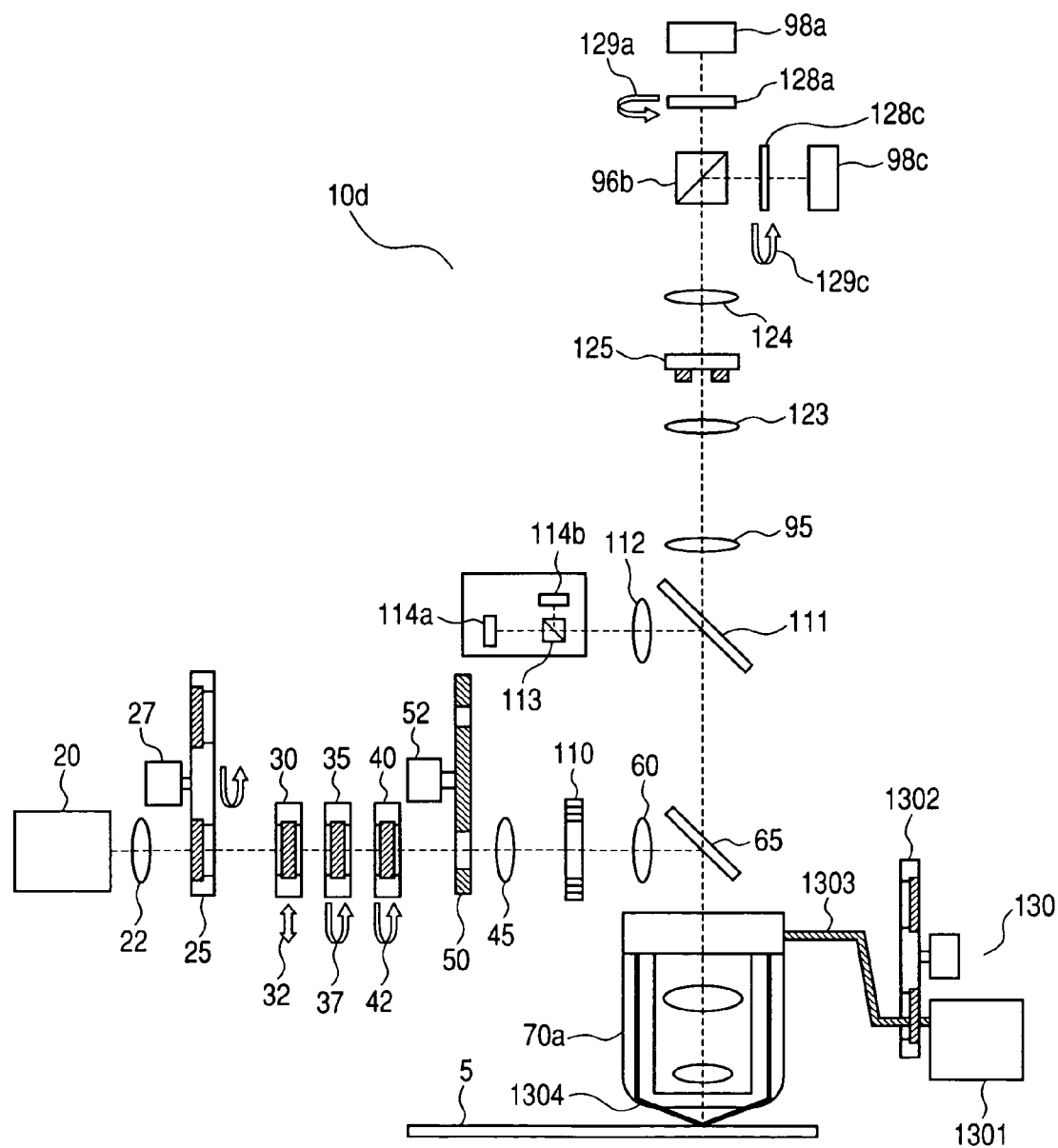
FIG. 4 is a front view showing an optical system configuration of an optical inspection apparatus according to a fourth embodiment of the present invention.

A fourth embodiment according to the present invention differs from the third embodiment in terms of configuration of an optical system 10d, as shown in FIG. 4. The optical system 10d differs from that in the third embodiment in that the wavelength bands of the visible light obtained from a dark-field illumination system and a dark-field illumination system are narrowed to range from, for example, about 400 nm to about 600 nm. The optical system 10d also differs in that a wavelength separation filter (dichroic mirror) 96a separates the light into two wavelength bands (e.g., one kind of light in a green band of about 500-600 nm is reflected and another kind of light in a blue band of about 400-500 nm is passed). Yet another difference is that image sensors 98c, 98a, and analyzers 128c, 128a are provided in association with the wavelength bands.

If the above image sensors 98c, 98a can receive light of the blue band and light of the green band, inspections can be performed on ordinary semiconductor devices. In addition, if the light is switched to UV light, the wavelength separation filter (dichroic mirror) 96a transmits the UV light and the image sensor 98a receives the light and outputs an image signal. Therefore, inspection with UV light is also possible.

As described above, according to the fourth embodiment, operational effects similar to/equivalent to those of the third embodiment can be obtained.

Fifth Embodiment

Figure 5:
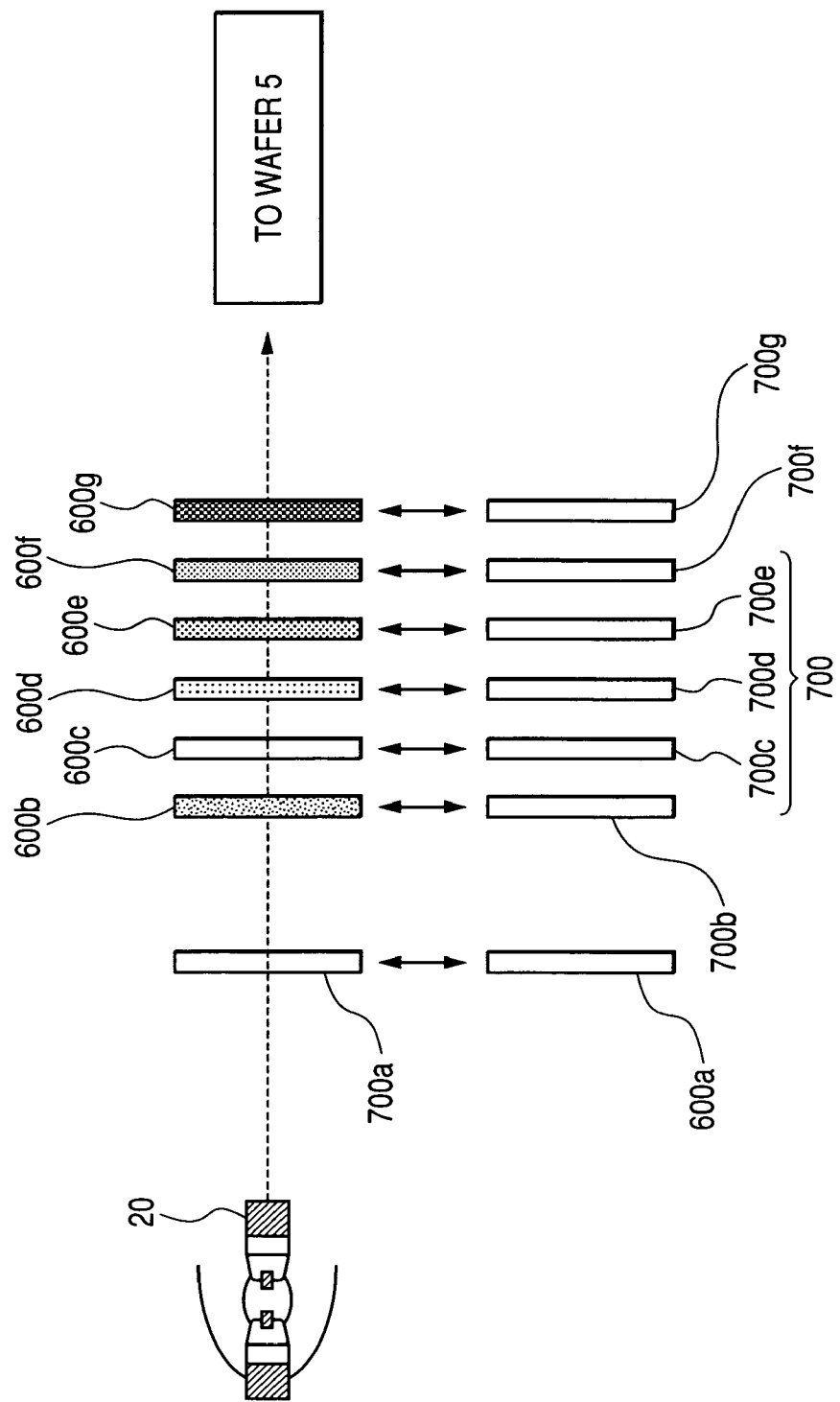
FIG. 5 is a diagram showing a large number of switchable band cutoff filters and optical path length compensation glass members of an optical inspection apparatus according to a fifth embodiment of the present invention.
Figure 6:
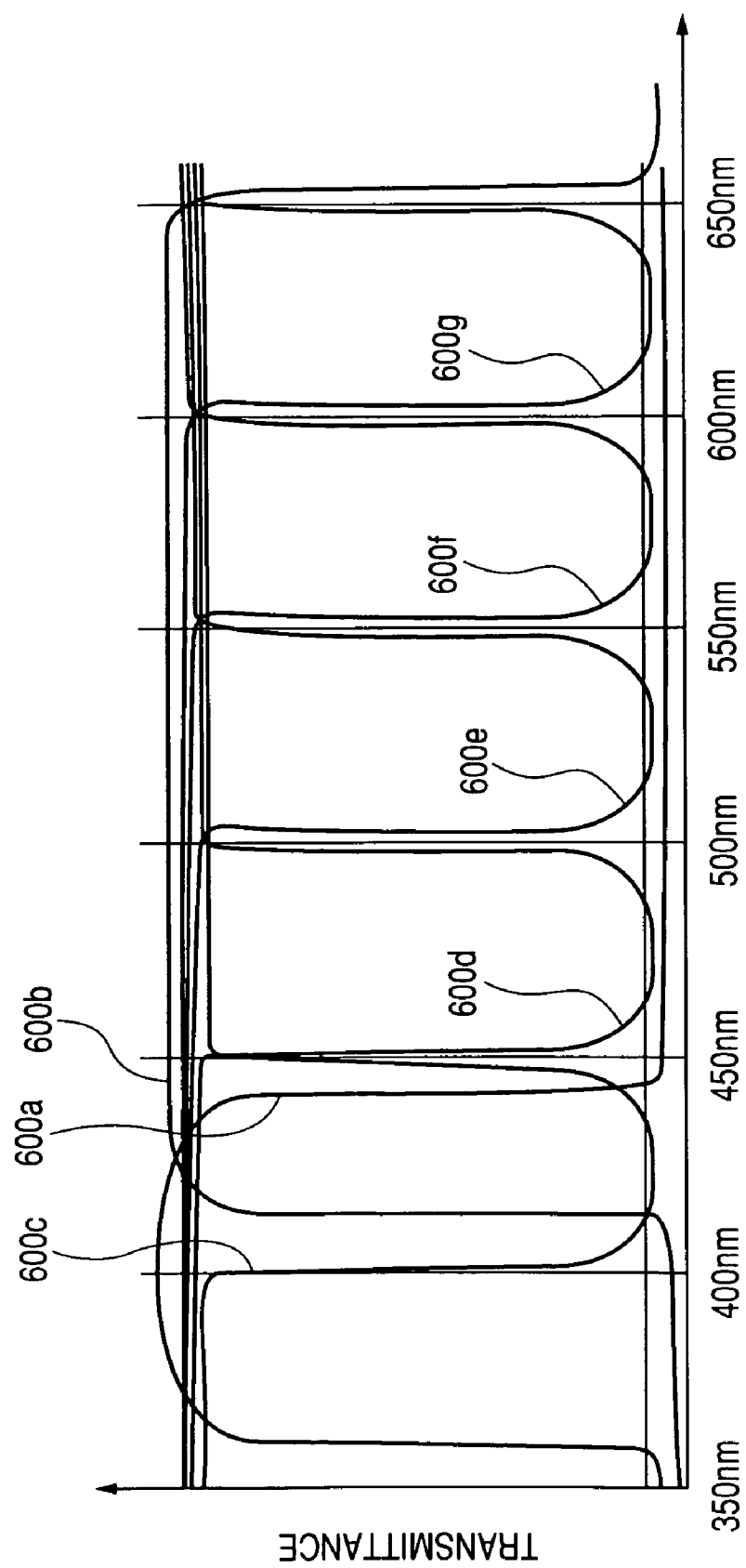
FIG. 6 is a diagram that shows spectral transmittance characteristics of the large number of switchable band cutoff filters of the optical inspection apparatus according to the fifth embodiment of the present invention.
Figure 7:
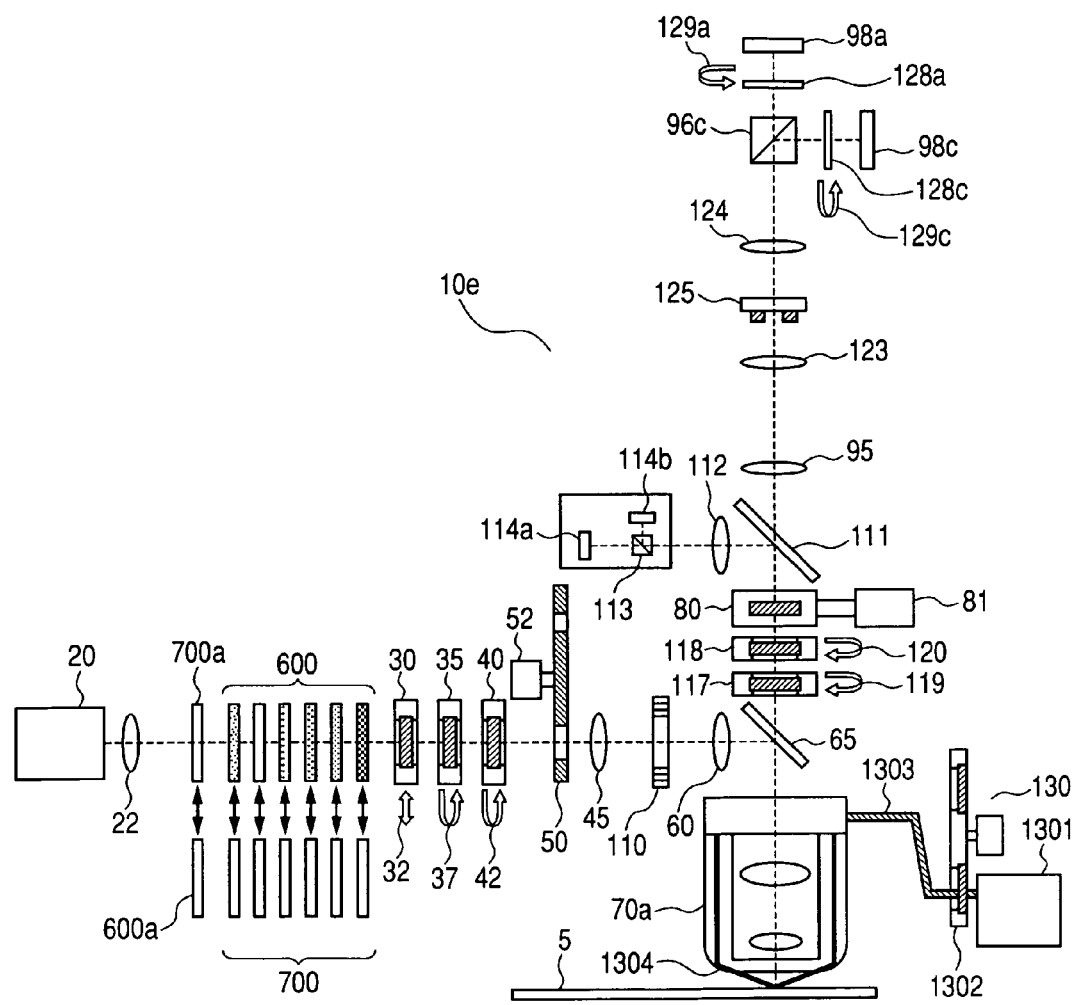
FIG. 7 is a front view showing an optical system configuration of the optical inspection apparatus according to the fifth embodiment of the present invention.

A fifth embodiment according to the present invention differs from the fourth embodiment in terms of configuration of an optical system 10e, as shown in FIGS. 5 to 7. FIG. 5 is a diagram showing a large number of band cutoff filters and a group of optical path compensation glass members which can be switched from one band cutoff filter to one glass member. FIG. 6 is a diagram that shows spectral transmittance characteristics of the band cutoff filters. The optical system 10e differs from the fourth embodiment's equivalent in the following aspects. That is to say, the wavelength separation filter 25 in the fourth embodiment is removed from a bright-field illumination system in the fifth embodiment. Instead, a large number of band cutoff filters, 600a to 600g, and a group of optical path compensation glass members 700a to 700g are selectably constructed so that a wavelength band can be selected for the pitch of about 40 to 60 nm or for twice the pitch, that is, for the pitch of about 80 to 120 nm or any multiple wavelength from a wide wavelength range (about 350 nm to about 700 nm). It is apparent that a wavelength selection filter 25 may be used instead of the band cutoff filter (UV selection filter) 600a and the band cutoff filter 600b.

As shown in FIG. 6, the band cutoff filter (UV selection filter) 600a is constructed of a filter adapted to shield light whose wavelengths are about 360 nm or less and about 440 nm or more, and transmit UV light and light of a purple wavelength whose wavelength ranges from about 360 nm to about 440 nm. The band cutoff filter 600b is constructed of a filter adapted to shield light whose wavelengths are about 420 nm or less and about 650 nm or more, and transmit visible light whose wavelengths are about 420 nm or more and about 650 nm or less. The band cutoff filter 600c is constructed of a filter adapted to shield the light having a purple wavelength from about 400 nm to about 450 nm, and transmit the light having other wavelengths. The band cutoff filter 600d is constructed of a filter adapted to shield the light having a blue wavelength from about 450 nm to about 500 nm, and transmit the light having other wavelengths. The band cutoff filter 600e is constructed of a filter adapted to shield the light having a green wavelength from about 500 nm to about 550 nm, and transmit the light having other wavelengths. The band cutoff filter 600f is constructed of a filter adapted to shield the light having a yellow wavelength from about 550 nm to about 600 nm, and transmit the light having other wavelengths. The band cutoff filter 600g is constructed of a filter adapted to shield the light having a red wavelength from about 600 nm to about 650 nm, and transmit the light having other wavelengths.

Therefore, UV light with a wavelength of about 340 to 400 nm can be obtained by, for example, using the band cutoff filters 600a and 600c, and purple light with a wavelength of about 420 to 450 nm can be obtained by, for example, using the band cutoff filters 600b and 600d to 600g. Blue light with a wavelength of about 450 to 500 nm can be obtained by, for example, using the band cutoff filters 600b, 600c, and 600e to 600g, and green light with a wavelength of about 500 to 550 nm can be obtained by, for example, using the band cutoff filters 600b, 600c, 600d, 600f, and 600g. Yellow light with a wavelength of about 550 to 600 nm can be obtained by, for example, using the band cutoff filters 600b, 600c to 600e, and 600g, and red light with a wavelength of about 600 to 650 nm can be obtained by, for example, using the band cutoff filters 600b and 600c to 600f. A wavelength band with a pitch of about 40 to 60 nm, a wavelength band with twice the foregoing pitch, that is, with a pitch of about 80 to 120 nm, or any multiple wavelength bands can be sequentially selected from a wide wavelength range (about 350 nm to about 700 nm). Based on the object to be inspected, any one of the three selection methods can be implemented so that defects of interest can be detected at high sensitivity and so that a detection ratio of false defects can be reduced below a reference value.

Receding the band cutoff filters 600a to 600g from an optical path of the illumination system generates subtle differences in optical path length, so the differences in optical path length can be compensated by inserting the optical path length compensation glass members 700a-700g.

A wavelength separation filter (dichroic mirror) 96c is disposed so that it can separate light into two wavelength bands (for example, by reflecting light of a green-to-red band of about 500 to 650 nm and transmitting the remaining light of a UV-to-blue band of about 350 to 500 nm). Also, image sensors 98c, 98a, and analyzers 128c, 128a are provided in association with the above wavelength bands. As a result, the image sensor 98c can receive the sequentially selected red light, yellow light, and green light obtained from the illuminated object under inspection, and the image sensor 98a can receive the sequentially selected blue light, purple light, and UV light obtained from the illuminated object under inspection.

As in the second embodiment of FIG. 2, an analyzer 80 installed on a rotatable mechanism 81 to transmit only oscillation components of a specific electric-field vector, a half-wave plate 117 rotationally controlled by a half-wave plate rotator 119, and a quarter-wave plate 118 rotationally controlled by a quarter-wave plate rotator 120 are included in the apparatus configuration shown in FIG. 7. Consequently, even under dark-field illumination conducted by a dark-field illumination system 130, control of the analyzer 80, half-wave plate 117, quarter-wave plate 118, and analyzers 128b, 128a, enables the image sensors 98a, 98b to receive light with a polarization azimuth (oscillation components of a specific electric-field vector) matched to the pattern formed on the object to be inspected.

As described above, according to the fifth embodiment, it is possible to select wavelength bands for illumination light at small pitches (e.g., from about 40 nm to about 60 nm) as well as to achieve operational effects similar to or equivalent to those obtained in the fourth embodiment.

Sixth Embodiment

Figure 8:
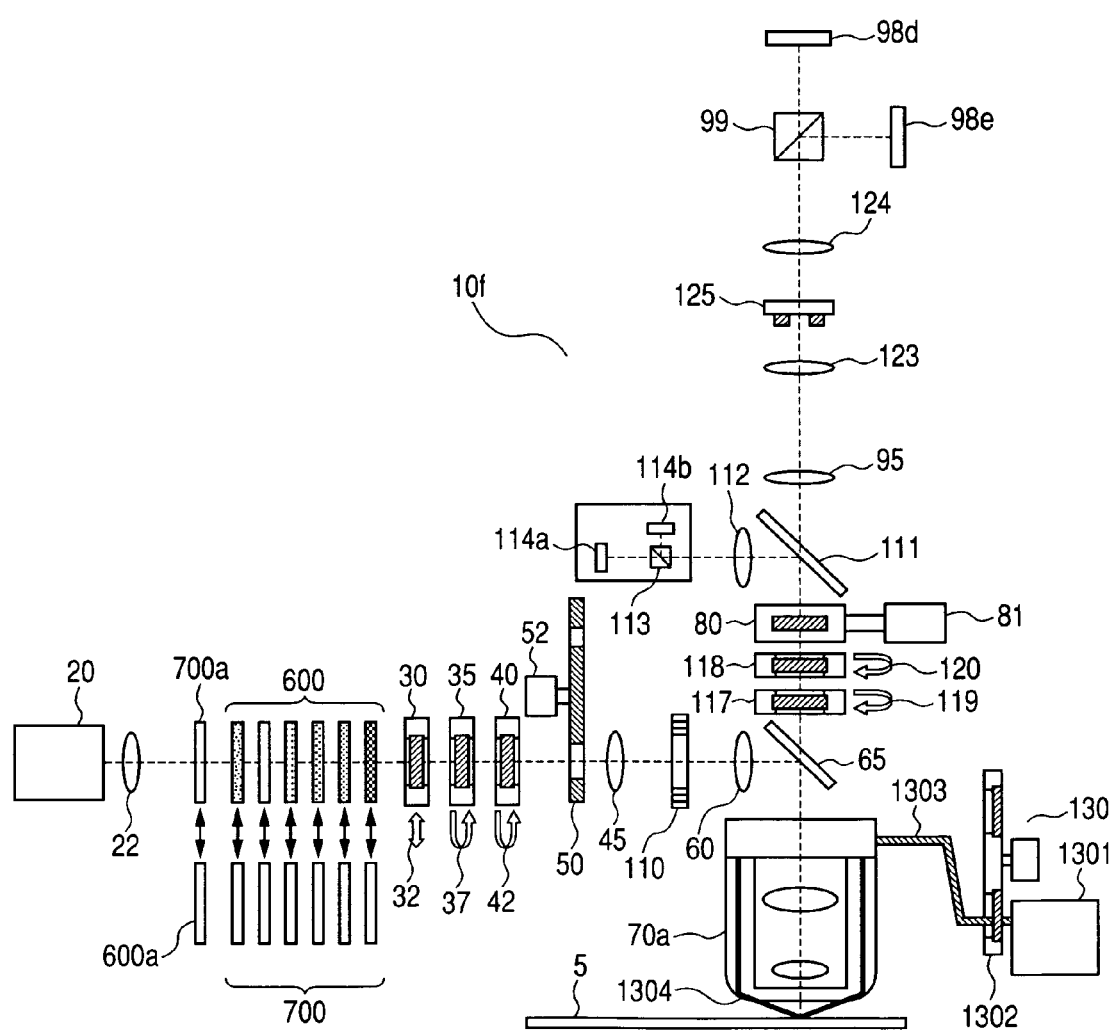
FIG. 8 is a front view showing an optical system configuration of an optical inspection apparatus according to a sixth embodiment of the present invention.

A sixth embodiment according to the present invention differs from the fifth embodiment in terms of configuration of an optical system 10f, as shown in FIG. 8. The optical system 10f differs from that in the fifth embodiment in that a polarizing beam splitter 99 is provided instead of the wavelength separation filter (dichroic mirror) 96c used in the fifth embodiment. The optical system 10f also differs in that the analyzers 128b, 128a in the fifth embodiment are removed, and in that whereas S-polarized light components separated by the polarizing beam splitter 99 are received by an image sensor 98d (TDI sensor included), P-polarized light components are received by an image sensor 98e (TDI sensor included). The image sensors 98d, 98e receive optical beams of a number of wavelength bands that have been sequentially selected for the pitch of about 40 to 60 nm and applied to the object to be inspected, and then the image sensors output associated image signals. Also, the image sensors 98d, 98e need to have sensitivity over a wide band.

As described above, according to the sixth embodiment, it is possible, during detection under dark-field illumination, to control a polarization azimuth similarly to the second embodiment, as well as to achieve operational effects similar to or equivalent to those obtained in the fifth embodiment.

Seventh Embodiment

A detailed description will be given below of a seventh embodiment relating to the high-sensitivity inspection parameter selection (high-sensitivity inspection parameterization) in the optical defect inspection apparatus configurations described in the first to sixth embodiments of the present invention. The functions and configurations of the optics in the optical defect inspection apparatus configurations of the present invention have been described. A larger number of functions and parameters, however, make it difficult to select parameters for high-sensitivity inspection (optical parameterization and image-processing parameterization) to routinely inspect wafers (inspection after pre-inspection).

Figure 11:
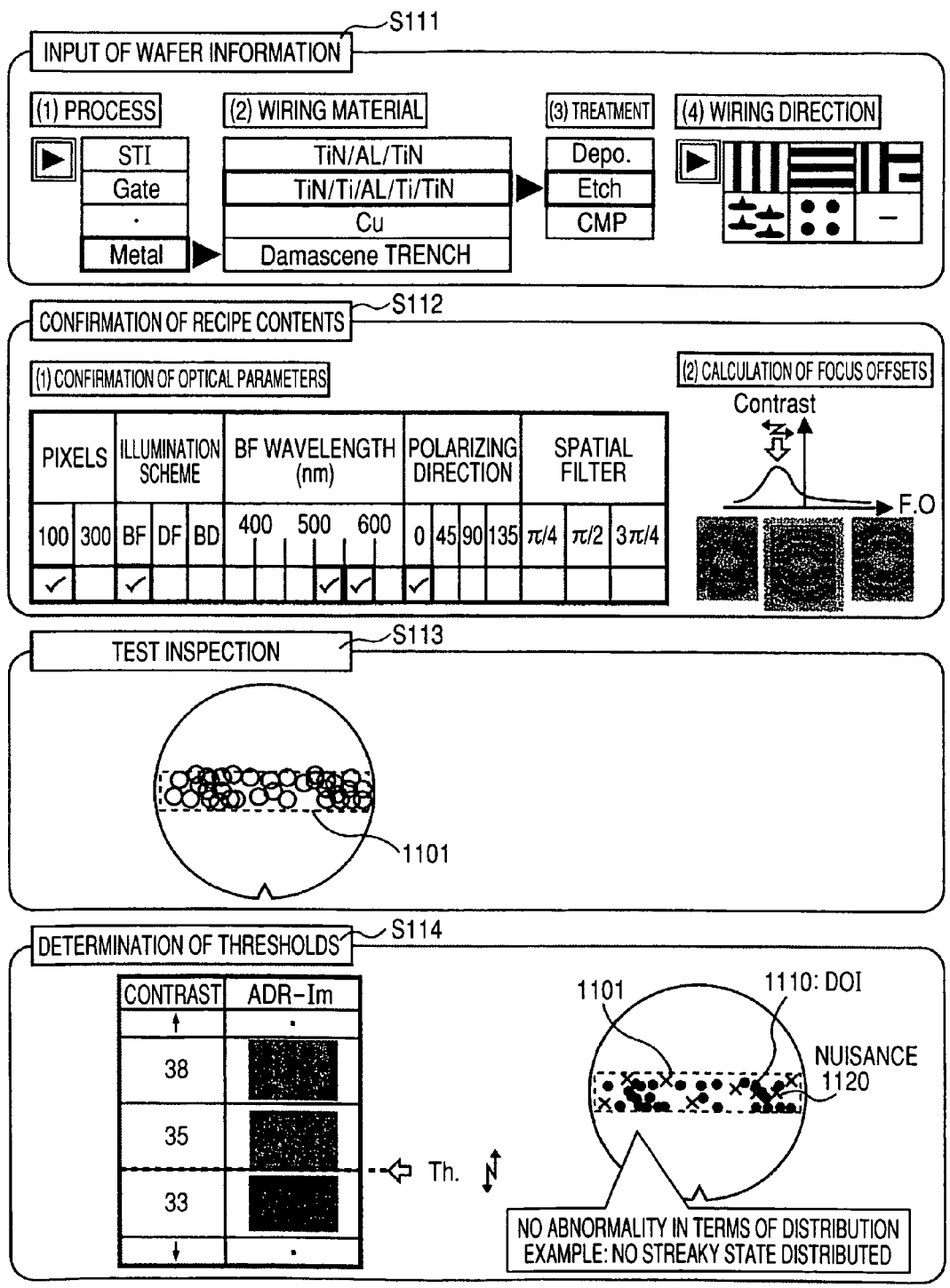
FIG. 11 is a diagram showing an example of a GUI screen for inspection parameter selection with a high-sensitivity selector in the present invention.
Figure 12:
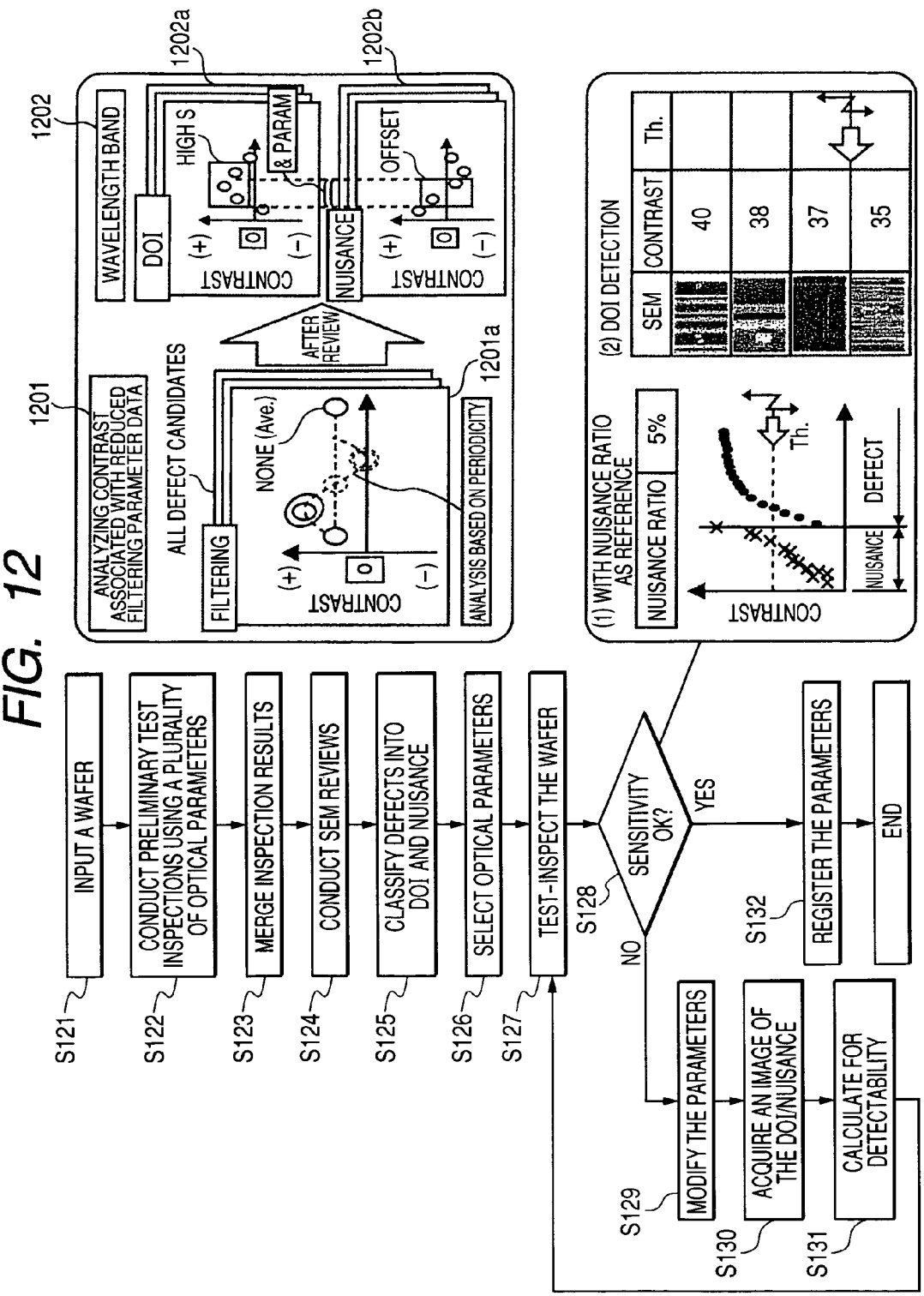
FIG. 12 is a diagram that shows a process flow for selection of inspection parameters (conditions) using the high-sensitivity selector in the present invention, details of processing for selection an optical parameter (condition), and items for judging sensitivity.

Accordingly, a more efficient process flow to select parameters for high-sensitivity inspection (optical parameterization and image-processing parameterization) in the optical defect inspection apparatus 1 of the present invention will be described hereunder using FIGS. 10, 11, and 12. FIG. 10 is a diagram that shows a link between the inspection information obtained in the optical defect inspection apparatus 1 as to a wafer to be subjected to parameterization, and the review result information obtained in a reviewing SEM device. FIG. 11 is a view showing the GUI section of the optical defect inspection apparatus that is used for parameterization. FIG. 12 is a diagram showing a more efficient process flow of selecting high-sensitivity inspection parameters.

First, a wafer 1001 for which parameters are to be set up is placed to the defect inspection apparatus 1 in step S121, as denoted by reference number 1010, and as shown in step S111 of FIG. 11, information on the wafer 1001 is input using an operating unit 320 (GUI section 3202) or the like. The wafer information to be input includes a product type, process information [(1) Process name (such as STI: Shallow Trench Isolation, Gate formation, or Metal wiring), (2) Wiring material (such as TiN/Al/TiN, TiN/Ti/Al/Ti/TiN, Cu, or Damascene), (3) Treatment (such as film deposition, etching, or CMP (Chemical-Mechanical Polishing), (4) Wiring direction (such as pattern direction)), a lot number, etc. Next, information on the array of dies formed on a wafer 5, information on memory cell areas of each die (i.e., device matrix), and other information are read out from a data server 330 and then designated using the operating section 320 (GUI section 3202) or the like. If this device matrix is already created in any other process, then the existing device matrix is copied. Next, information on coordinates for θ-alignment of the wafer 5 with respect to a view field of an optical system 10a to 10f and XY stages 210, 211, and information on a target mark for alignment are input using the operating section 320 or the like.

Next in step S122, preliminary test inspections in a test region 1101 are sequentially conducted using, among all functions and parameters (conditions) of the optical system 10a to 10f, only predetermined optical initial parameters convenient for detecting diverse defects. These initial parameters relate to, for example, wavelength bands [(for the optical system 10a to 10c, four parameter sets; for the optical system 10d, two parameter sets; and for the optical system 10e to 10f, six parameter sets) plus two polarization azimuth parameter sets plus two spatial filter parameter sets]]. The preliminary test inspections are conducted using pixels larger than the pixels (pixel size corresponding to a single pixel of the image sensor that is placed above a wafer) used during the routine inspection (main inspection). Thus, for a preliminary test inspection for a fixed area of the wafer (i.e., the fixed area of the wafer is the test region 1101 that is a local region in the wafer shown in test inspection step S113 of FIG. 11), the inspection time required can be shortened to $1/(\text{preliminary test pixel size/main inspection pixel size})^2$ and hence the overall time required for the preliminary test inspection can be correspondingly reduced.

The optical parameters that allow an DOI and nuisances to be separated can be estimated with a high margin by searching the following information: the optical parameters and defect information (brightness difference levels, defect image feature quantities, defect images, etc.) when were executed in the past inspections concerning the same product type and process whose information is stored within the inspection information DB 3301 of the inspection apparatus 1 shown in FIG. 10; and the parameter setup information that was used for detecting the defect, that is, information on the settings of optical parameters and contrast characteristics information of the DOI and nuisances according to the settings of optical parameters (e.g., wavelength bands and contrast characteristics of the DOI and nuisances according to the wavelength bands, and polarization filtering and contrast characteristics information of DOI and nuisances according to the polarization filtering). Thus, optical initial parameters can be narrowed down. Effective use of both the past inspection information and the past parameter setup information improves efficiency of parameter setup for inspecting finely structured wafers based on fine design rules. Effective use of the two sets of past information further contributes to the narrowing-down of the optical initial parameters (optical default parameter settings), on the result, the preliminary test inspection time can be reduced in step S122 shown in FIG. 12.

Next in step S123, the defect candidates that were detected using all of the optical initial parameters predetermined in the optical system 10a-10f and the image processor 300 are merged as one set of inspection results in the inspection information database (DB) 3301, shown in FIG. 10, of the data server 330. During the merge, since there are defect candidates where the same defect is detected by using plural sets of optical parameters, these defect candidates are defined as one defect candidate by matching against coordinates of the defect candidates. At this time, the appropriate inspection information is left in the above-merged set of inspection results so that which optical parameter set was used to detect the defect candidate can be identified.

To establish inspection parameters, in particular, preliminary test inspection results need to be checked against the review results within the SEM reviewing device 350 so that whether the preliminary test inspection results are for a DOI or a false defect can be judged. If the SEM review results can be displayed and confirmed using the GUI section 320b of the optical defect inspection apparatus 1, therefore, efficiency of parameter setup for the inspection apparatus 1 can be correspondingly improved.

Accordingly, the parameterization target wafer 1001 is unloaded from the defect inspection apparatus 1, as denoted by reference number 1011, and input to the reviewing SEM device 350, as denoted by 1020. At the same time, the host system (integrated inspection information system) 1000 supplies the above-merged set of inspection results (inspection target DB 3310 containing the product type, process information, lot number, defect candidate coordinates, etc.) from the data server 330 to the reviewing SEM (Scanning Electron Microscopic) device 350. In step S124, the reviewing SEM device 350 reviews the defect candidate of the parameter setup target wafer in accordance with the merged set of inspection results (especially, position coordinates of the defect candidate). In step S125, the reviewing SEM device 350 determines whether the defect candidate is a DOI (or the like) that want to be detected or a false defect (nuisance not influencing the yield) that may not be detected, and classifies the defect candidate properly. Additionally in step S125, classified review results (DOI/nuisance classification result, associated ADR images, and countermeasure information on causes of occurrence of the defect) are stored into the review result DB 3501, regardless of whether the review results are saved in the reviewing device. Furthermore, the parameterization target wafer 1001 is unloaded from the reviewing SEM device 350, as denoted by reference number 1021, and the above review results are supplied to the host system 1000 and stored into the optical parameter DB of the inspection information DBs 3301 in the data server 330.

An operator confirms the review information that has been stored into the optical parameter DB, by using the GUI section 320b of the defect inspection apparatus 1, and selects a yield-influential defect (DOI) or a defect to be detected which requires detection for process monitoring. For a nuisance, the operator also confirms an associated review image using the GUI section 320b of the defect inspection apparatus 1 and specifies that the defect be excluded from detection. This makes it possible for the defect inspection apparatus 1 to classify, as a DOI or a nuisance, the defect candidate that was detected using multiple sets of initial optical parameters for the parameter setup target wafer.

In addition, if the review results indicate that detection sensitivity or a detection ratio of nuisances is too low, the parameter setup target wafer 1001 is unloaded from the reviewing device 350 and reinput to the defect inspection apparatus 1 in order to provide for adjustment of the inspection parameters. After the adjustment of the inspection parameters, adequacy of the test inspection results can be analyzed by judging the nuisance detection ratio for appropriateness after matching against the coordinates of previously reviewed defects. Since no review results exist for any new defects detected after the adjustment of the inspection parameters, only unreviewed defect candidates are reviewed by the reviewing device 350 and review results obtained are stored into the review result DB 3501. The review results are also supplied to the host system 1000 and stored into the optical parameter DB of the inspection information DBs 3301 in the data server 330.

The following describes the optical parameter selection process step (S126) of FIG. 12 that is executed in the high-sensitivity inspection parameter selector 303 of the defect inspection apparatus 1. In step S126, the high-sensitivity inspection parameter selector (high-S/N-ratio inspection parameter selector) 303 in the image processing unit 300 selects optical parameters that make a DOI easily detectible and make nuisances difficult to detect. More specifically, the optical parameters here mean: (1) illumination scheme such as brightfield illumination BF, darkfield illumination DF, or brightfield/darkfield mixed illumination BD; detection wavelength band such as a detection wavelength band for brightfield illumination; polarization azimuth; spatial filter phase difference (0 to $\lambda$) or transmittance (0% to 100%); and pixel size. Also, the selection of the optical parameters is based on the optical parameter DB obtained during the preliminary test inspections using the optical initial parameters (optical default parameter settings) stored within the inspection information DBs of the data server 330. The optical parameter DB here relates to relationships between the illumination scheme and the contrast characteristics shown in terms of DOI contrast, between an optical parameter (wavelength band) and contrast characteristics shown in terms of DOI contrast (brightness difference), between the optical parameter (wavelength band) and the contrast characteristics shown in terms of nuisance contrast (brightness difference), and between optical parameters (filtering parameters) and the contrast characteristics shown in terms of contrast (brightness difference) of all defect candidates.

An example of a first step to select optical parameters effective for obtaining higher inspection sensitivity is by extracting the parameters that generate relatively high contrast for the DOI. An example of a second step is by extracting the parameters that generate relatively low contrast for the nuisance. Of these parameters, only the parameter that increases an inspection margin (=defect contrast−nuisance contrast) overlaps with other parameters. For this reason, recommending this parameter as an optical parameter to the operator enables accurate judgment of high-sensitivity inspection parameters.

The selection of an illumination scheme may also be based on what kind of defect is to be detected (e.g., whether a pattern defect or a foreign substance defect is to be detected) from the object. The high-sensitivity inspection parameter selector 303 calculates contrasts (brightness differences) of the defect candidates on the basis of the brightfield images, the darkfield images, and the brightfield/darkfield mixed images between the defect portion and a compared reference portion for the defect candidate which has been classified as a DOI after reviews, and selects calculated contrast data an illumination scheme advantageous for the detection of the DOI from the calculated contrasts (brightness differences) of the defect candidates. The configuration of the optical system for detecting the brightfield images, the darkfield images, and the brightfield/darkfield mixed images, has been detailed in the second embodiment of FIG. 2. For the brightfield/darkfield mixed images, predictions can likewise be conducted by, for example, detecting the brightfield image and the darkfield image and summing up both images.

A wavelength band 1202 is selected in the manner described below. For the optical systems 10a-10d described in the first to fourth embodiments of FIGS. 1 to 4, respectively, the wavelength bands of the light which the image sensors 98a-98c receive are determined by the wavelength bands separated by the wavelength separation filters (dichroic mirrors) 96a-96b. For each kind of object to be inspected, therefore, a plurality of characteristic DOIs 1202a (such as electrical shorting defects, chip defects, residue defects, or voids) are preferably selected in the test region 1101. Image signals obtained from the image sensors that receive the light of the wavelength bands at which the contrast of the above-selected DOIs 1202a is high are also preferably selected. In addition, and after selection of nuisances 1202b, image signals obtained from the image sensors that receive the light of the wavelength bands at which the contrast of the selected nuisances 1202b is low are preferably selected.

Figure 13:
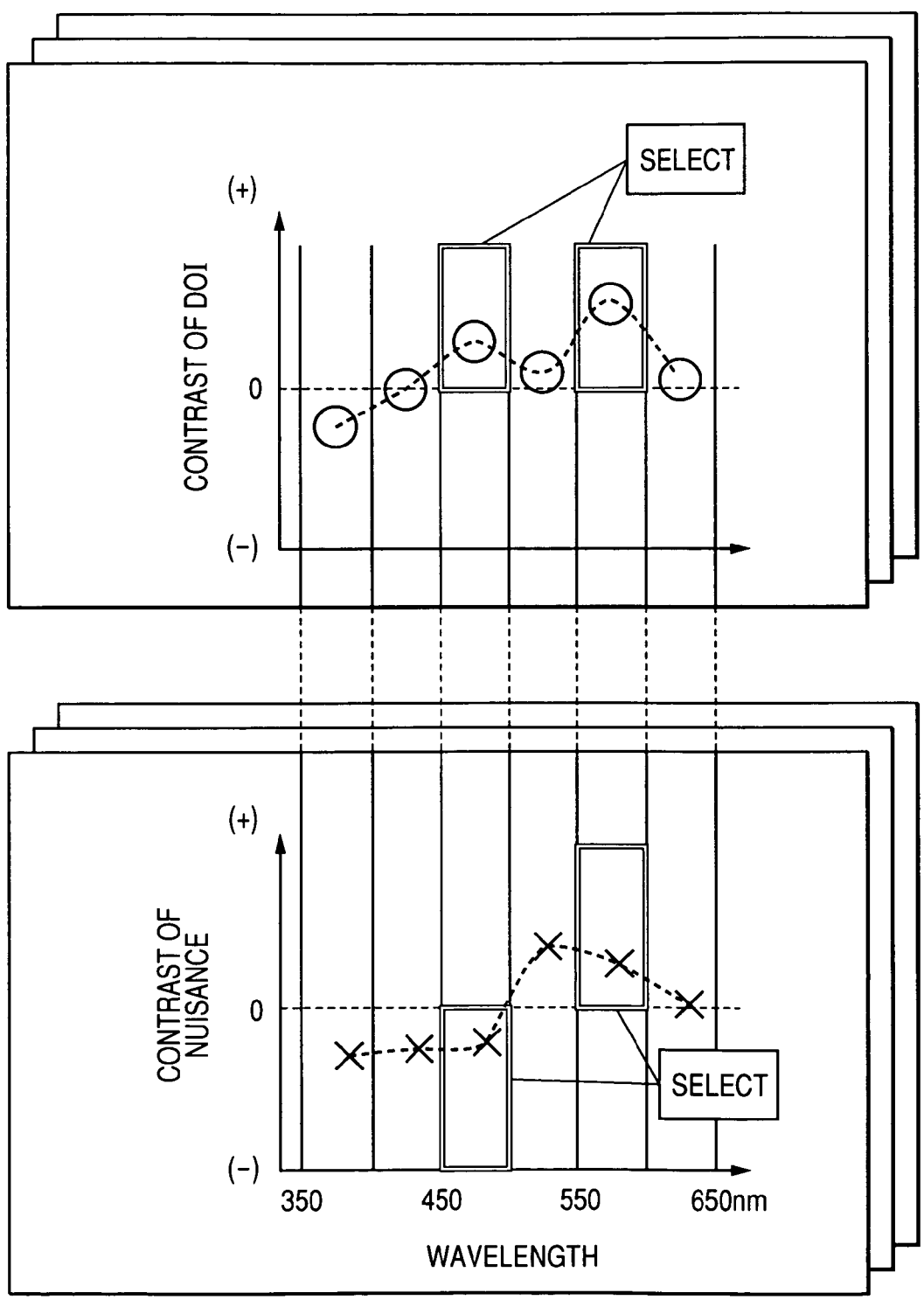
FIG. 13 is a diagram for describing a method of selecting a wavelength, which is one of optical parameters in the present invention.

In the fifth and sixth embodiments of FIGS. 7 and 8, respectively, since the wavelength band can be sequentially changed at pitches of, for example, about 40-60 nm, a plurality of characteristic DOIs 1202a (such as electrical shorting defects, chip defects, residue defects, or voids) can be selected in the test region 1101 for each kind of object to be inspected. In addition, it is possible to calculate, as shown in FIGS. 12 and 13, the contrast of each DOI 1202a on a wavelength band basis for each pitch so that polarity associated with the contrast can also be identified (i.e., whether the defect is darker (−) or brighter (+) than a normal portion can also be understood). Furthermore, it is possible to select wide wavelength band parameters (e.g., 450 to 500 nm and 550 to 600 nm) that enable high-contrast detection of the DOIs (in this case, the contrast of the DOIs becomes relatively high).

After a plurality of nuisances 1202b have been selected similarly, the contrast of these nuisances 1202b is calculated, as shown in FIGS. 12 and 13, on a wavelength band basis for each pitch so that polarity (−), (+) associated with the contrast can also be identified. Since the contrast of nuisances is based on the brightness change caused by, for example, thin-film interference due to a very insignificant change in film thickness of an interlayer dielectric film, as the illumination wavelength band is changed at small pitches, differences in contrast between the nuisances will be caused by the relationship with the film thickness change, and thus the wavelength bands that cancel out one another will exist. For these reasons, such wavelength bands that cancel out one another (e.g., 450 to 500 nm and 550 to 600 nm) can be selected as a wavelength band parameter that makes the contrast of the nuisances relatively low. That is to say, using a narrow wavelength band results in the contrast of the nuisances being increased by the thin-film interference due to the film thickness change, and no inspection margin is likely to be present in any narrow wavelength bands. If no inspection margin is present or when a greater margin is desired, after the polarity associated with the contrast of the nuisances has been examined, wide wavelength bands in which the polarity changes (or the polarities of the nuisances cancel out one another) are preferably extracted (selected). Illuminating the intended object with the light of the extracted wide wavelength bands averages the brightness obtained from the nuisances, correspondingly lessening the contrast thereof, and thus augmenting the inspection margin so as to prevent the nuisances from being detected at less than a predetermined nuisance detection ratio.

As described above, there is a need not merely to focus attention only on nuisance portions, but also to confirm that when the object is illuminated with the light of plural wavelength bands, a decrease spread of the contrast of the DOI does not decrease below a decrease spread of the contrast of the nuisances. Thus, the parameters that allow a defect margin to be expanded can be selected by simultaneously illuminating a wide wavelength bandwidth that includes multiple wavelength bands (e.g., 450 to 500 nm and 550 to 600 nm).

Next, filter selection is described below. The selection of filters includes selecting a combination of polarizing filters (35, 40, 80, 117, 118, 128a-128c) and selecting a spatial filter 125. The parameter that generates the greatest allowable margin for the high contrast obtained from defect candidates is likewise selected for both the polarizing filters and the spatial filter. However, there are a number of combinations of polarizing filters, and a combination with the spatial filter is also required, so the need arises to consider diversified factors in selecting each filter. On one hand, the polarization azimuths in the polarizing filters and the phase difference, for example, in the spatial filter, both have periodicity as the contrast detected from the defect candidates, since each polarization azimuth and the phase difference suffer rotation changes with respect to the direction of the wiring pattern. Therefore, if the direction of a filter that increases a contrast level denoted by the double circle to its maximum with reference to no filtering can be calculated for the filter 1201a shown in FIG. 12, it is also possible to calculate from the above periodicity the direction of a filter that generates, for example, a contrast level denoted by the dotted-circle with reference to no filtering, and the direction of a filter that reduces, for example, a contrast level denoted by the dotted double circle to its minimum. That is to say, for a filter (polarizing filter and phase difference filter) 1201a, contrast data on a number of defect candidates can be detected with periodicity, so even if the contrast (brightness difference) is grasped by thinning out filtering direction, parameters can be set up by estimating an optimum direction of the polarizing filter (e.g., polarizer 128a-128c) and the phase difference of the phase difference filter. For the transmittance filter that is one kind of spatial filter, however, the way of thinning out contrast will be optionally determined, since contrast with periodicity cannot be detected from defect candidates.

As described above, after contrast data on a plurality of characteristic defect candidates are calculated with filtering parameter thinned out and then storing the calculated contrast data into the optical parameter DB, it becomes necessary to predict and select the filtering parameters that generate the highest allowable contrast over the plurality of characteristic defect candidates, on the basis of the stored contrast data, and periodicity, of the plural characteristic defect candidates.

Next in step S127, in the high-sensitivity inspection parameter selector 303, a pixel size is set to match the parameter to be used during the main inspection, other optical parameters are automatically calculated or user-selected as basic ones, and the test inspection is executed. The test inspection results obtained at the pixel size used during the main inspection are most likely to include defects that were not subjected to SEM reviewing. If it is to be confirmed whether the SEM-unreviewed defects are defects to be detected or false defects not to be detected, these defects may be SEM-reviewed for the confirmation. To conduct more efficient SEM reviews, automatic classification results by the optical defect inspection apparatus 1 of the present invention may be used to SEM-review only typical defects falling under an accurately classified, highly established category.

Next in step S131, results of the test inspection denoted as step S113 in FIG. 11 are checked against SEM-reviewed DOIs 1110 and nuisances 1120 for coordinate matching. After this, images of any matched DOIs and nuisances, the images to be compared with these images, image feature quantities (such as contrast) of the DOIs, and others are evaluated and analyzed. Based on these evaluations and analyses, automatic calculations are conducted in step S114 of FIG. 11 to obtain the image-processing parameters (e.g., discrimination threshold levels) that make the DOIs and the nuisances discriminatable in the most convenient form, that is, so as to cause no distribution errors (e.g., no distribution of streaks prone to detection as false defects from an edge of a normal pattern). The image-processing parameters that have thus been automatically calculated are used to display information of the defect candidates that have been determined as the DOIs, at the operating section 320. The information includes, for example, information on SEM review images and on the reviewed and determined DOIs and nuisances.

In step S128, the high-sensitivity inspection parameter selector 303 uses the above information to conduct the following determinations, for example, as shown in FIG. 12:

(1) Determining with a nuisance detection ratio as its reference whether a rate of the nuisances is within an allowable range (2) Determining whether sensitivity is good enough for the detected DOI [SEM image (ADR image) and contrast] displayed at the GUI section 320b If the sensitivity and/or the rate of the nuisances is found to be in an unallowable range, the high-sensitivity inspection parameter selector 303 conducts step S129 to modify any optical parameters likely to increase the sensitivity or reduce the rate of the nuisances, among all optical parameters predicted from those which were modified during the test inspection, and from preliminary test inspection results. In step S130, the optical system 10 and the image processing unit 300 use the above-predicted optical parameters to acquire DOI and nuisance images and associated comparison reference images at the pixel size to be used during the main inspection. In this case, the images of the DOIs and those of the nuisances may be acquired by imaging these defects with a two-dimensional camera (not shown) that is different from the image sensor used during actual inspection. The reason is that, since the image sensor 98 used during actual inspection is a linear sensor, the stages need to be moved at an equal speed to acquire images of specific coordinates, and thus the image acquisition time required tends to prolong in comparison with the time required for image acquisition with the two-dimensional camera. To the user, however, the image acquisition time may not become a problem, so the linear image sensor 98 may be used to acquire the images. In particular, if spectral sensitivity and/or pixel size significantly differ between the image sensor 98 and the above-mentioned two-dimensional camera, it is preferable that the image sensor 98 be used to acquire the images.

Next, the high-sensitivity inspection parameter selector 303 uses the above-acquired DOI and nuisance images to calculate the optical parameters and image-processing parameters used for generating the most desirable sensitivity and nuisance detection ratio. After that, it is automatically calculate in step S131 whether detection sensitivity and nuisance detection ratio of target defect are allowable for optimum optical parameters and image-processing parameters. If automatic calculation results fall within an allowable range, step S127 is conducted to use the above optimum parameters and execute test inspections at the pixel size to be used during the main inspection. If test inspection results fall outside an allowable range, processing is returned to step S129, in which step the optical parameters are then modified once again and then the images of the DOIs and nuisances and the reference image for comparison are acquired to improve the optical parameters and the image-processing parameters.

Results of the test inspection that has been repeated again at the pixel size to be used during the main inspection are also checked against SEM review results, and the image-processing parameters are improved as necessary. After improvement of any image-processing parameters, judgments are conducted on appropriateness of the inspection sensitivity and that of the nuisance detection ratio. If no problem is detected, parameter setup is completed and SEM-reviewed defect information (such as a defect size, classification results, and the causes of the defect) is registered in the inspection information databases 3301 of the data server 330 in step S132.

These databases are utilized to establish new parameters relating to, for example, semiconductor wafers that employ the same product type, the same process, or the same semiconductor material.

As described above, the high-sensitivity inspection parameter selector 303 confirms inspection parameter settings (recipe contents) in step S112 of FIG. 11 and optimizes a combination between: (1) optical parameters [pixel size, illumination scheme (brightfield illumination BF, darkfield illumination DF, brightfield/darkfield mixed illumination BD, or the like), detection wavelength band (such as a detection wavelength band based on brightfield illumination), polarization azimuth, and the phase difference, transmittance, and illumination σ parameters (including an out-of-focus aperture stop parameter) of the spatial filter]; (2) Focus offset calculations and others for calculating the offsets needed to focus light on a desired circuit pattern layer; and image-processing parameters for easy discrimination of DOIs and nuisances, such as discrimination threshold levels.

The above combination is optimized using the DOI and nuisance images and image feature quantities obtained when preliminary test inspections were conducted using the optical initial parameters (optical default parameter settings) stored within the data server 330. The DOI/nuisance discrimination performance assuming the use of the optimized image-processing parameters is calculated and a combination between the image-processing parameters and the optical parameters that provide the easiest method of DOI detection and allow suppression of nuisance detection is determined from calculation results. Alternatively, the calculation results are displayed at the operating section (GUI section) 320, as shown in recipe contents confirmation step S112 of FIG. 11, in such a format as to allow selection by the apparatus user. In this case, since combinations between multiple sets of optical parameters [listed under (1) Optical parameter confirmation] and image-processing parameters are to be displayed, SEM images of the DOIs and defect candidates detected using various inspection parameters acquired from the reviewing SEM device via a host system 340 are preferably displayed together for easy selection of parameters.

According to the present invention, the optical parameters that improve the contrast of the defects to be detected (defects of interest: DOI) and reduce the nuisance detection ratio of nuisances to a value less than a reference can be selected within a minimum time according to a particular kind of inspection object (target) on a semiconductor wafer. Highly sensitive and rapid inspection can therefore be implemented.

According to the present invention, a plurality set of optical parameters for maximizing an image acquisition ratio of desired defects of interest (DOI) according to a particular kind of inspection object (target) on the semiconductor wafer can also be searched for within a minimum time.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes that come within the meaning and range of equivalency of the claims are therefore intended to be embraced therein.

What is claimed is:

1. An optical inspection apparatus, comprising:
a light source which emits light of a wide wavelength band;
an illumination optical system which irradiates an object to be inspected that is formed on a sample with the light of the wide wavelength band that is emitted from the light source;
a detection optical system which includes a wavelength separation element and a plurality of image sensors, the wavelength separation element being formed such that reflection light having the wide wavelength band obtained from the object on the sample with which the light has been irradiated by the illumination optical system is separated into plural light paths by the wavelength bands, each of a plurality of image sensors is positioned in respective optical paths of the reflection light separated by the wavelength separation element and receiving optical image of each of the reflection lights separated by the wavelength separation element so as to output each of image signals; and
an image processing unit which detects defects of interest;
wherein the image processing unit selects a desired image signal which suppresses detection of false defects according to kind of the object to be inspected, from the image signals obtained from the plurality of image sensors in the detection optical system, and detects the defects of interest by processing the selected image signal.

2. The optical inspection apparatus according to claim 1, wherein a plurality of objective lenses whose aberration has been corrected for each of the plurality of wavelength bands in the wide wavelength band are each selectably disposed for common use in the illumination optical system and the detection optical system.

3. The optical inspection apparatus according to claim 1, wherein the illumination optical system further includes:
a bright-field illumination optics that irradiates the sample with the light having the plurality of wavelength bands; and
a dark-field illumination optics that irradiates the sample with the light having the plurality of wavelength bands.

4. The optical inspection apparatus according to claim 1, wherein the light of the wide wavelength band that is emitted from the light source includes visible light.

5. The optical inspection apparatus according to claim 4, wherein the illumination optical system further includes a band cutoff filter group constructed such that light of a plurality of any wavelength bands is selected from a wavelength band of visible light by combining a plurality of band cutoff filters which cut off lights of different specific wavelength bands.

6. The optical inspection apparatus according to claim 1, wherein the light of the wide wavelength band that is emitted from the light source includes visible light and ultraviolet (UV) light.

7. The optical inspection apparatus according to claim 6, wherein the illumination optical system further includes a band cutoff filter group constructed such that light of a plurality of any wavelength bands is selected from wavelength bands of visible light and UV light by combining a plurality of band cutoff filters which cut off lights of different specific wavelength bands.

8. The optical inspection apparatus according to claim 7, wherein the illumination optical system further includes a wavelength selection element that selects each of UV light and visible light by switching between the UV light and the visible light.

9. The optical inspection apparatus according to claim 1, wherein:
the illumination optical system further includes a polarizing control optics that controls a polarization state of the irradiated light; and
the detection optical system includes at least an analyzer.

10. The optical inspection apparatus according to claim 1, wherein:
the illumination optical system further includes a polarizing control optics that controls the polarization state of the irradiated light; and
the detection optical system includes an analyzer between the wavelength separation element and each of the image sensors.

11. The optical inspection apparatus according to claim 9, wherein the wavelength separation element includes a polarizing beam splitter disposed to split the UV light and the visible light.

12. The optical inspection apparatus according to claim 1, further comprising:
an objective lens for common use in the illumination optical system and the detection optical system; and
a controllable or selectable spatial filter disposed at a position conjugate to a pupil of the objective lens in the detection optical system.

13. An optical inspection apparatus, comprising:
a light source which emits light of a wide wavelength band;
an illumination optical system having a wavelength selection optical element which selects light having a plurality of wavelength bands from the light of the wide wavelength band that is emitted from the light source, wherein the illumination optical system irradiates an object to be inspected that is formed on a sample, with the light that has been selected by the wavelength selection optical element;
a detection optical system that includes a wavelength separation element and a plurality of image sensors, the wavelength separation element being formed such that reflection light having the plurality of wavelength bands obtained from the object to be inspected on the sample that has been irradiated by the illumination optical system with the light is separated into plural light paths by the wavelength band, and each of the plurality of image sensors is positioned in respective optical paths of the reflection light separated by the wavelength separation element and receiving optical image of each of the reflection lights that have been separated by the wavelength separation element so as to output each of image signals; and an image processing unit which detects defects of interest;
wherein:
the wavelength selection optical element of the illumination optical system selects the light of a desired wavelength band which suppresses detection of false defects according to kind of the object to be objected; and
the image processing unit processes an image signal selected from the image signals obtained from each of the image sensors in the detection optical system so as to detect the defects of interest.

14. The optical inspection apparatus according to claim 13, wherein:
the illumination optical system further includes a polarizing control optics adapted to control a polarization state of the irradiated light; and
the detection optical system includes an analyzer between the wavelength separation element and each of the image sensors.

15. The optical inspection apparatus according to claim 14, further comprising:
an objective lens for common use between the two optical systems in the illumination optical system and the detection optical system; and
a spatial filter controllably or selectably disposed at a position conjugate to a pupil of the objective lens in the detection optical system.

16. An optical inspection apparatus, comprising:
a light source which emits light of a wide wavelength band;
an illumination optical system having a wavelength selection optical element which selects light having a plurality of wavelength bands from the light of the wide wavelength band that is emitted from the light source, wherein the illumination optical system irradiates an object to be inspected that is formed on a sample, with the light that has been selected by the wavelength selection optical element;
a detection optical system which includes a polarizing separation element and a plurality of image sensors, the polarizing separation element being formed such that reflection light having the plurality of wavelength bands obtained from the object to be inspected on the sample that has been irradiated by the illumination optical system with the light is separated into plural light paths by polarization states, each of the plurality of image sensors is positioned in respective optical paths of the reflection light separated by the polarizing separation element and receiving optical image of each of the reflection lights that have been separated by the polarizing separation element so as to output each of image signals; and
an image processing unit which detects defects of interest;
wherein:
at least the illumination optical system or the detection optical system further has a polarizing control optics which controls polarization states;
the wavelength selection optical element of the illumination optical system selects the light of a desired wavelength band which suppresses detection of false defects according to kind of the object to be inspected; and
the image processing unit detects the defects of interest by processing an image signal selected from the image signals obtained from each of the image sensors in the detection optical system.

17. An optical inspection method, comprising:
an illumination step of irradiating an object to be inspected that is formed on a sample, with light of a wide wavelength band that is emitted from a light source that emits the light of the wide wavelength band, by an illumination optical system;
a detection step of separating reflection light having a wide wavelength band obtained from the object to be inspected on the sample irradiated with the light in the illumination step, into plural light paths by the wavelength band, by a wavelength separation element and receiving optical image of the reflection light separated by the wavelength separation element, by each of a plurality of image sensors which is positioned in respective optical paths of the reflection light separated by the wavelength separation element so as to output each of image signals; and
an image processing step of detecting defects of interest in an image processing unit;
wherein the image processing step includes the sub-steps of:
selecting a desired image signal which suppresses detection of false defects according to kind of the object to be inspected from the image signals obtained from the plurality of image sensors in a detection optical system; and
detecting the defects of interest by processing the selected image signal.

18. The optical inspection method according to claim 17, wherein, in the illumination step, the illumination optical system uses a bright-field illumination optics adapted to irradiate the object to be inspected with the light having the plurality of wavelength bands and a dark-field illumination optics adapted to irradiate the object to be inspected with the light having the plurality of wavelength bands.

19. The optical inspection method according to claim 17, wherein, in the illumination step, the light of the wide wavelength band emitted from the light source includes visible light.

20. The optical inspection method according to claim 19, wherein, in the illumination step, the illumination optical system includes a band cutoff filter group constructed such that light of a plurality of any wavelength bands is selected from a wavelength band of visible light by combining a plurality of band cutoff filters which cut off lights of different specific wavelength bands.

21. The optical inspection method according to claim 17, wherein:
in the illumination step, a polarizing optics that controls a polarization state of the irradiated light is used as the illumination optical system; and
in the detection step, an analyzer controllably arranged between the wavelength separation element and each of the image sensors is used.

22. An optical inspection method, comprising:
an illumination step of selecting light of a plurality of wavelength bands from light of a wide wavelength band that is emitted from a light source that emits the light of the wide wavelength band, by a wavelength selection optical element and irradiating an object to be inspected that is formed on a sample, with the selected light of the plural wavelength bands;
a detection step of separating reflection light having a plurality of wavelength bands obtained from the object to be inspected on the sample irradiated with the light in the illumination step, into plural light paths by the wavelength band and receiving optical image of the reflection light having each of the wavelength bands separated by wavelength separation element, by each of plural image sensors which is positioned in respective optical paths of the reflection light separated by the wavelength separation element so as to output each of image signals; and an image processing step of detecting defects of interest in an image processing unit;

wherein:

in the illumination step, the wavelength selection optical element selects the light of the desired wavelength band which suppresses detection of false defects according to kind of the object to be inspected; and in the image processing step, an image signal selected from the image signals obtained from the image sensors in the detection step is processed so as to detect the defects of interest.

23. An optical inspection method, comprising:

an illumination step of selecting light having a plurality of wavelength bands from the light of a wide wavelength band that is emitted from a light source that emits the light of the wide wavelength band, and irradiating an object to be inspected that is formed on a sample, with the selected light of the plural wavelength bands;

a detection step of separating reflection light having the plurality of wavelength bands obtained from the object to be inspected on the sample irradiated with the light in the illumination step, into plural light paths by the wavelength band by a wavelength separation element and receiving optical image of each of the reflection lights that have been separated by the wavelength separation element, by a plurality of image sensors which is positioned in respective optical paths of the reflection light separated by the wavelength separation element so as to output each of image signals; and an image processing step of detecting defects of interest in an image processing unit;

wherein:

at least in the illumination step or the detection step, a polarizing control optics which can control a polarization state is used;

in illumination step, the wavelength selection optical element selects light of a desired wavelength band which suppresses detection of a false defect according to kind of the object to be inspected; and in the image processing step, an image signal selected from the image signals obtained from the image sensors in the detection step is processed so as to detect the defects of interest.

* * * * *